(12) United States Patent
Conklin

(10) Patent No.: US 8,845,720 B2
(45) Date of Patent: Sep. 30, 2014

(54) PROSTHETIC HEART VALVE FRAME WITH FLEXIBLE COMMISSURES

(75) Inventor: Brian S. Conklin, Orange, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 13/237,556

(22) Filed: Sep. 20, 2011

(65) Prior Publication Data

US 2012/0078357 A1 Mar. 29, 2012

Related U.S. Application Data

(60) Provisional application No. 61/386,833, filed on Sep. 27, 2010, provisional application No. 61/472,083, filed on Apr. 5, 2011.

(51) Int. Cl.
*A61F 2/24* (2006.01)

(52) U.S. Cl.
USPC .......................... 623/2.14; 623/2.18; 623/2.38

(58) Field of Classification Search
USPC ................................. 623/2.1, 2.12–2.19, 2.38
See application file for complete search history.

(56) References Cited

U.S. PATENT DOCUMENTS

| | | |
|---|---|---|
| 3,143,742 A | 8/1964 | Cromie |
| 3,320,972 A | 5/1967 | High et al. |
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |

(Continued)

FOREIGN PATENT DOCUMENTS

| | | |
|---|---|---|
| CN | 2356656 Y | 1/2000 |
| EP | 84395 A1 | 7/1983 |

(Continued)

OTHER PUBLICATIONS

Krakow,"3F Therapeutics,Inc. Announces the First Clinical Implantation of the 3F Enable Aortic Heart Valve™, a Patented, Sutureless Implantation, Replacement Heart Valve Intended to Save Valuable Surgery Time and Reduce Time Related Complications . . . " Healthcare Sales & Marketing Network News Feed, Jan. 18, 2005, pp. 1 2.

(Continued)

*Primary Examiner* — Randy Shay
(74) *Attorney, Agent, or Firm* — AnneMarie Kaiser; Guy Cumberbatch

(57) ABSTRACT

A prosthetic heart valve can include a valve frame having a wireform portion and a stent portion. The wireform and stent portions can be undetachably coupled together via a plurality of upright struts so as to form a one-piece prosthetic heart valve frame. Alternatively, a self-expanding wireform portion and a balloon-expandable stent portion can be coupled together via one or more leaflets and a subassembly having a flexible leaflet support stent and a sealing ring. The wireform portion can include cusps and commissures configured to support a plurality of leaflets. The prosthetic valve can be radially collapsible for minimally invasive and/or transcatheter delivery techniques. Disclosed embodiments can also provide flexion of the wireform portion (e.g., of the commissures) in response to physiologic pulsatile loading when the valve is implanted in a patient's native valve annulus. Methods of making and using prosthetic heart valves are also disclosed.

17 Claims, 19 Drawing Sheets

(56) References Cited

U.S. PATENT DOCUMENTS

| | | |
|---|---|---|
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,552 A | 5/1995 | Andersen et al. |
| 5,413,676 A | 5/1995 | Nguyen et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A * | 7/1999 | Huynh et al. ................ 623/2.14 |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,371,983 B1 | 4/2002 | Lane |
| 6,376,845 B1 | 4/2002 | Purtle |
| 6,402,780 B2 | 6/2002 | Williamson, IV et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,530,952 B2 | 3/2003 | Vesely |
| 6,558,418 B2 | 5/2003 | Carpentier et al. |
| 6,558,429 B2 | 5/2003 | Taylor |
| 6,569,196 B1 | 5/2003 | Vesely |
| 6,582,462 B1 | 6/2003 | Andersen et al. |
| 6,585,766 B1 * | 7/2003 | Huynh et al. ................ 623/2.38 |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,719,789 B2 | 4/2004 | Cox |
| 6,730,118 B2 | 5/2004 | Spenser et al. |
| 6,733,525 B2 | 5/2004 | Yang et al. |
| 6,736,845 B2 | 5/2004 | Marquez et al. |

(56) References Cited

U.S. PATENT DOCUMENTS

| | | |
|---|---|---|
| 6,764,508 B1 | 7/2004 | Roehe et al. |
| 6,767,362 B2 | 7/2004 | Schreck |
| 6,786,925 B1 | 9/2004 | Buchanan et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,846,325 B2 | 1/2005 | Liddicoat |
| 6,893,459 B1 | 5/2005 | Macoviak |
| 6,893,460 B2 | 5/2005 | Spenser et al. |
| 6,908,481 B2 | 6/2005 | Cribier |
| 6,936,067 B2 | 8/2005 | Buchanan |
| 6,939,365 B1 | 9/2005 | Fogarty et al. |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,025,780 B2 | 4/2006 | Gabbay |
| 7,070,616 B2 | 7/2006 | Majercak et al. |
| 7,081,131 B2 | 7/2006 | Thornton |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,172,625 B2 | 2/2007 | Shu et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| 7,311,730 B2 | 12/2007 | Gabbay |
| RE40,377 E | 6/2008 | Williamson, IV et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,468,073 B2 | 12/2008 | Johnson et al. |
| 7,470,285 B2 | 12/2008 | Nugent et al. |
| 7,513,909 B2 | 4/2009 | Lane et al. |
| 7,534,261 B2 | 5/2009 | Friedman |
| 7,556,647 B2 | 7/2009 | Drews et al. |
| 7,569,072 B2 | 8/2009 | Berg et al. |
| 7,578,843 B2 | 8/2009 | Shu |
| 7,585,321 B2 | 9/2009 | Cribier |
| 7,597,711 B2 | 10/2009 | Drews et al. |
| 7,611,535 B2 | 11/2009 | Woolfson et al. |
| 7,682,390 B2 | 3/2010 | Seguin |
| 7,758,632 B2 | 7/2010 | Hojeibane et al. |
| 7,780,726 B2 | 8/2010 | Seguin |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0078950 A1 | 4/2004 | Schreck |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1* | 9/2004 | Schreck ............. 623/2.18 |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1* | 6/2005 | Haug et al. ............. 623/2.11 |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0149181 A1 | 7/2005 | Eberhardt |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0136054 A1 | 6/2006 | Berg et al. |
| 2006/0149360 A1 | 7/2006 | Schwammenthal et al. |
| 2006/0154230 A1 | 7/2006 | Cunanan et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |

(56) References Cited

U.S. PATENT DOCUMENTS

| | | |
|---|---|---|
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1* | 12/2006 | Rowe et al. ............ 623/2.18 |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0050021 A1 | 3/2007 | Johnson |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1* | 10/2007 | Francis ............ 623/1.26 |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0004688 A1 | 1/2008 | Spenser et al. |
| 2008/0021546 A1 | 1/2008 | Patz et al. |
| 2008/0033543 A1 | 2/2008 | Gurskis et al. |
| 2008/0065198 A1 | 3/2008 | Quintessenza |
| 2008/0119875 A1 | 5/2008 | Ino et al. |
| 2008/0249619 A1 | 10/2008 | Stacchino et al. |
| 2008/0275540 A1 | 11/2008 | Wen |
| 2008/0281411 A1 | 11/2008 | Berreklouw |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0036484 A1 | 2/2010 | Hariton et al. |
| 2010/0049313 A1 | 2/2010 | Alon et al. |
| 2010/0082094 A1* | 4/2010 | Quadri et al. ............ 623/1.26 |
| 2010/0161028 A1* | 6/2010 | Chuter et al. ............ 623/1.13 |
| 2010/0161036 A1 | 6/2010 | Pintor et al. |
| 2010/0249894 A1 | 9/2010 | Oba et al. |
| 2011/0147251 A1 | 6/2011 | Hodshon et al. |
| 2011/0282439 A1* | 11/2011 | Thill et al. ............ 623/2.17 |

FOREIGN PATENT DOCUMENTS

| | | |
|---|---|---|
| EP | 0084395 A1 | 7/1983 |
| EP | 96721 A1 | 12/1983 |
| EP | 0125393 A1 | 11/1984 |
| EP | 0143246 A2 | 6/1985 |
| EP | 171059 A1 | 2/1986 |
| EP | 0179562 A1 | 4/1986 |
| EP | 1171059 A1 | 1/2002 |
| GB | 2056023 A | 3/1981 |
| GB | 2069843 A | 9/1981 |
| GB | 2254254 A | 10/1992 |
| GB | 2279134 A | 12/1994 |
| SU | 1116573 A1 | 7/1985 |
| SU | 1697790 A1 | 12/1991 |
| WO | 8900840 A1 | 2/1989 |
| WO | 9115167 A1 | 10/1991 |
| WO | 9212690 A1 | 8/1992 |
| WO | 9213502 A1 | 8/1992 |
| WO | 9219184 A1 | 11/1992 |
| WO | 9219185 A1 | 11/1992 |
| WO | 9517139 A1 | 6/1995 |
| WO | 9528899 A1 | 11/1995 |
| WO | 9640006 A1 | 12/1996 |
| WO | 9709933 A1 | 3/1997 |
| WO | 9709944 A1 | 3/1997 |
| WO | 9727799 A1 | 8/1997 |
| WO | 9741801 A1 | 11/1997 |
| WO | 9742871 A1 | 11/1997 |
| WO | 9806329 A1 | 2/1998 |
| WO | 99/11201 A2 | 3/1999 |
| WO | 9915112 A1 | 4/1999 |
| WO | 9951169 A1 | 10/1999 |
| WO | 0032105 A1 | 6/2000 |
| WO | 0040176 A1 | 7/2000 |
| WO | 00/60995 A2 | 10/2000 |
| WO | 01/54624 A1 | 8/2001 |
| WO | 01/54625 A1 | 8/2001 |
| WO | 02076347 | 10/2002 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

\* cited by examiner

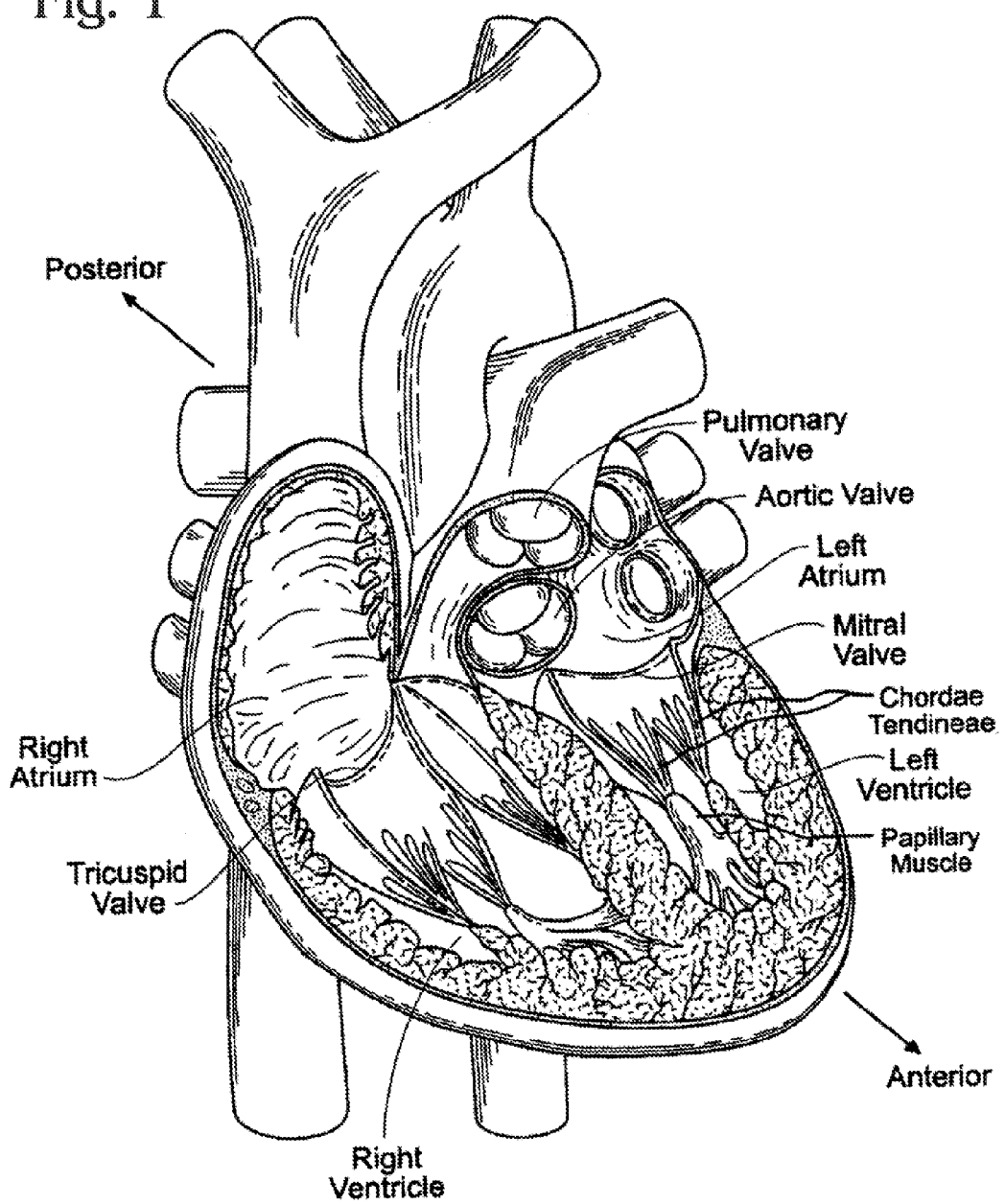

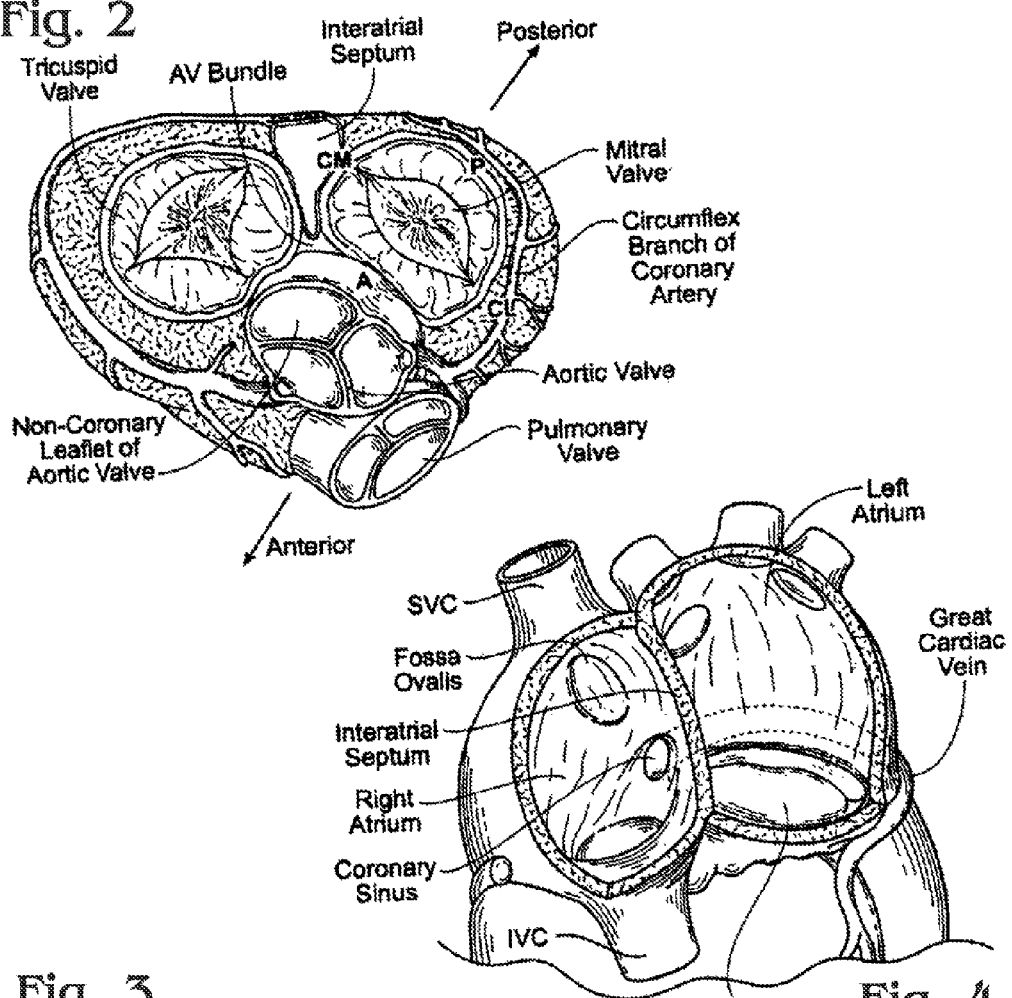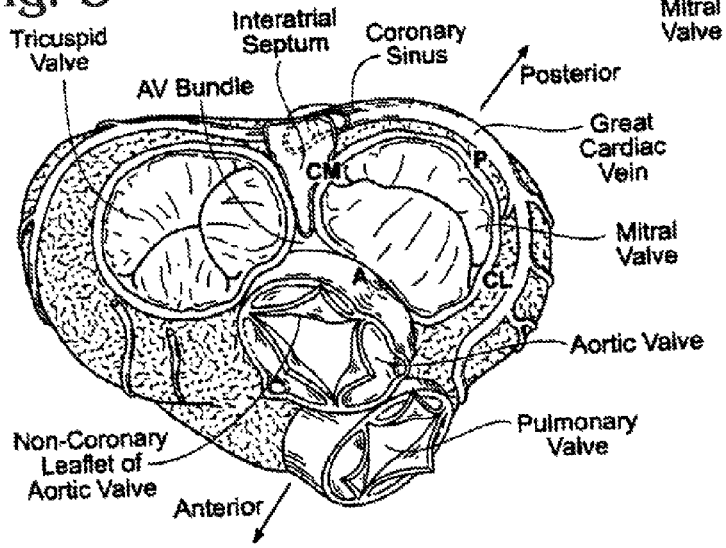

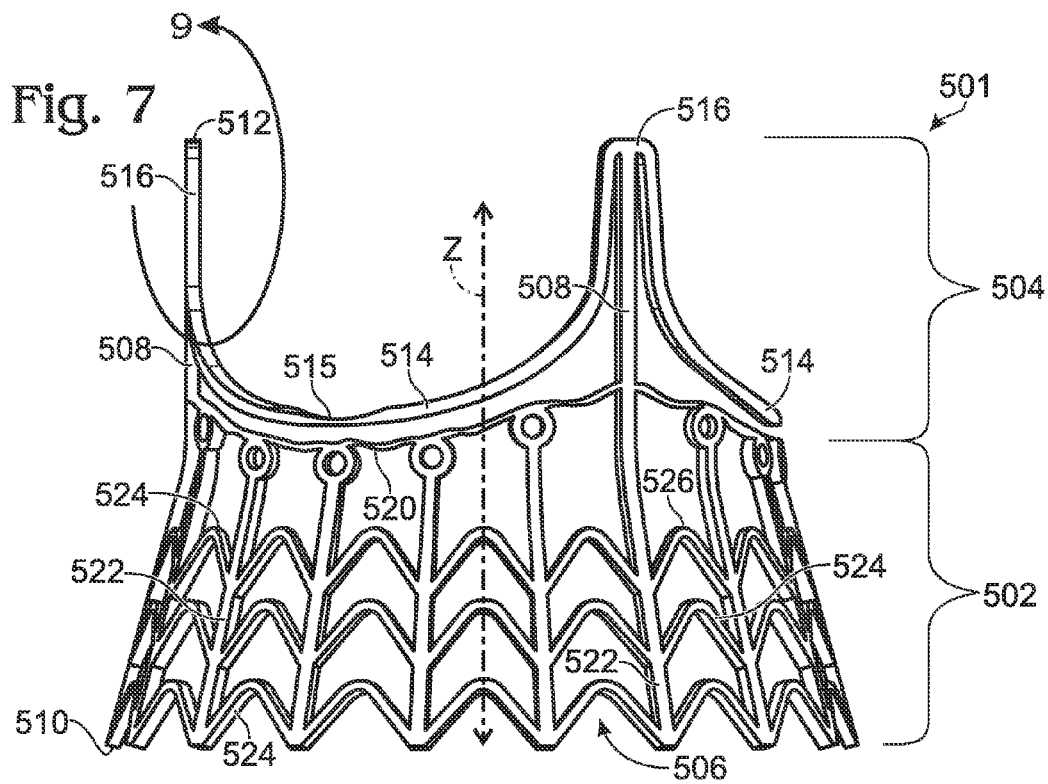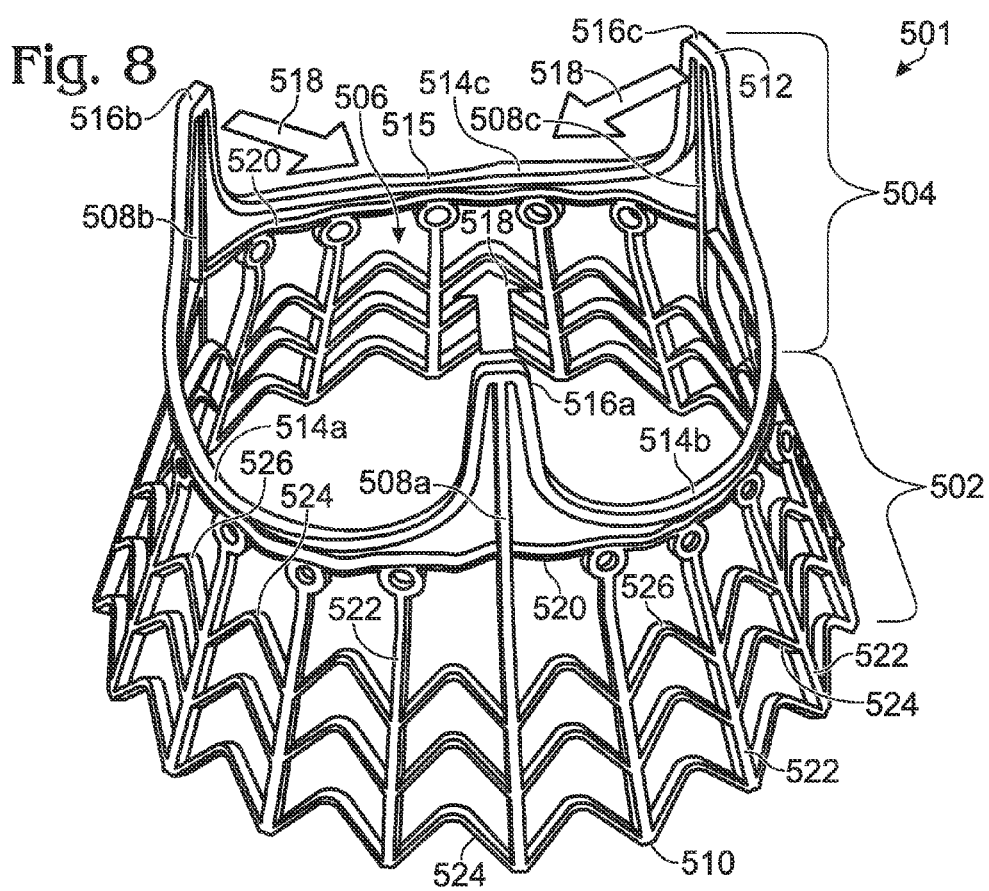

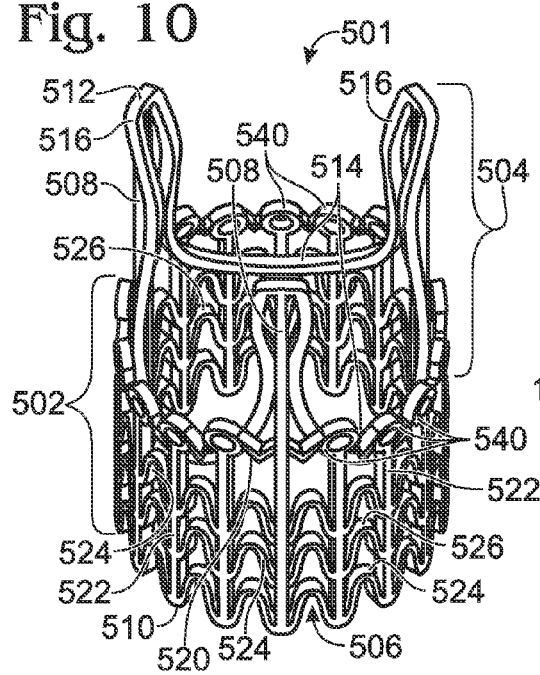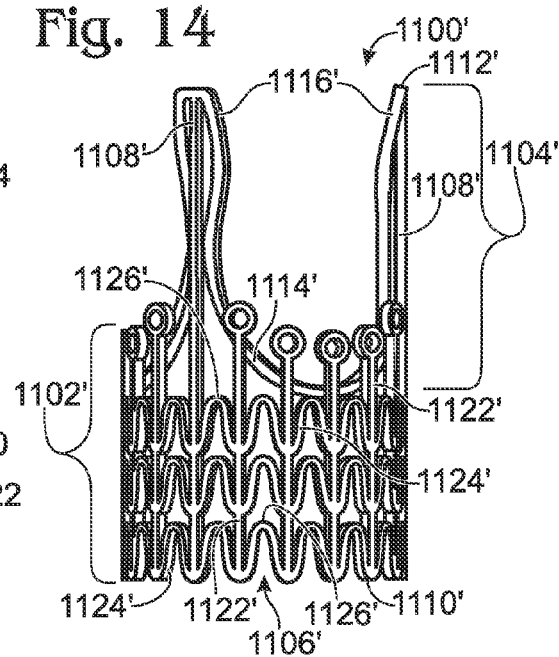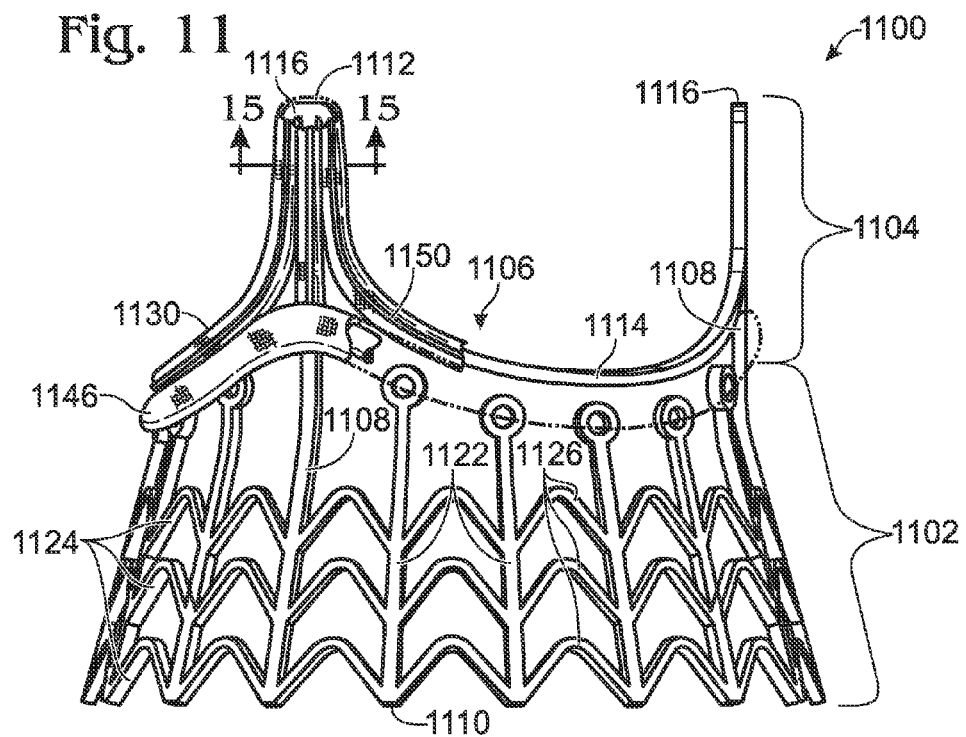

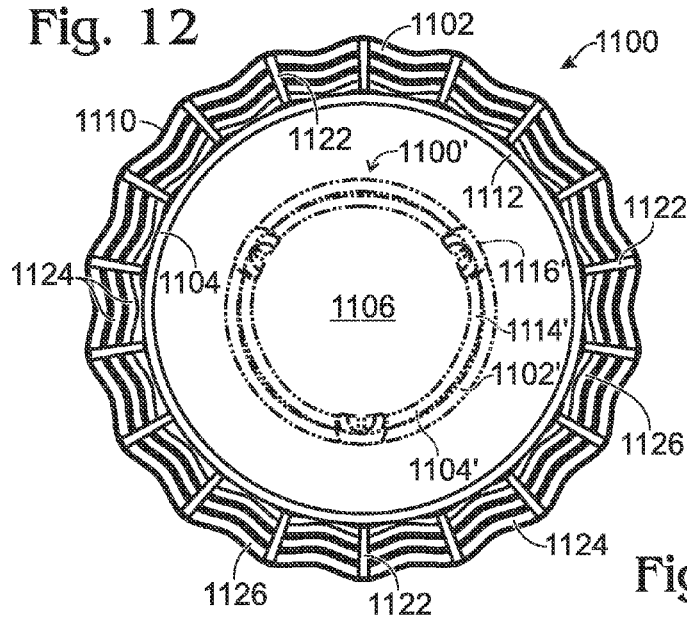
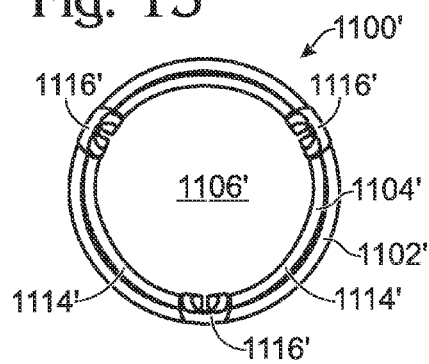
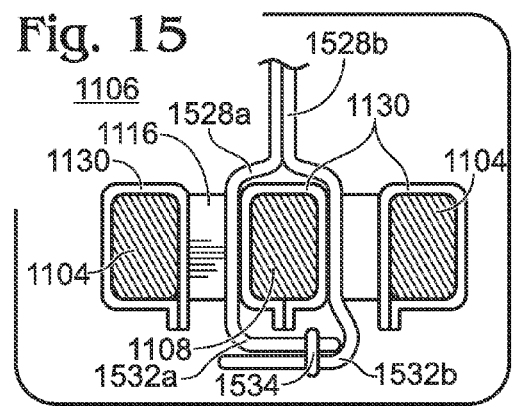
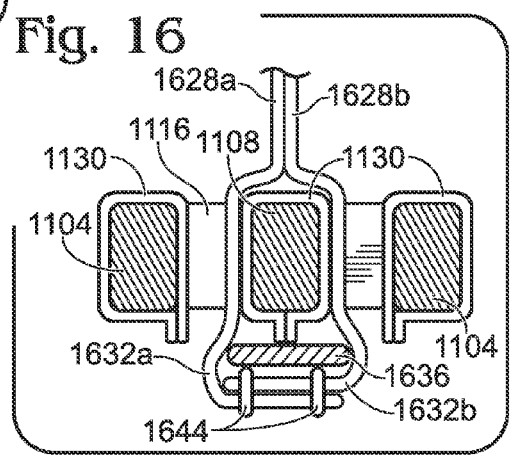

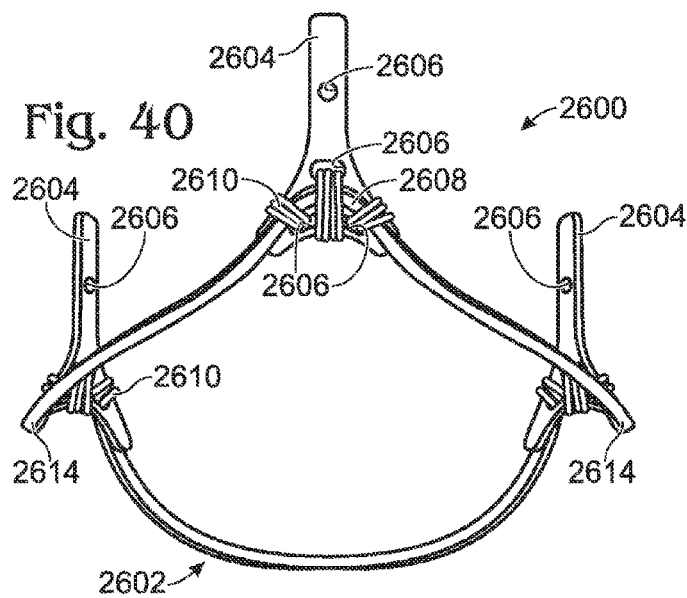
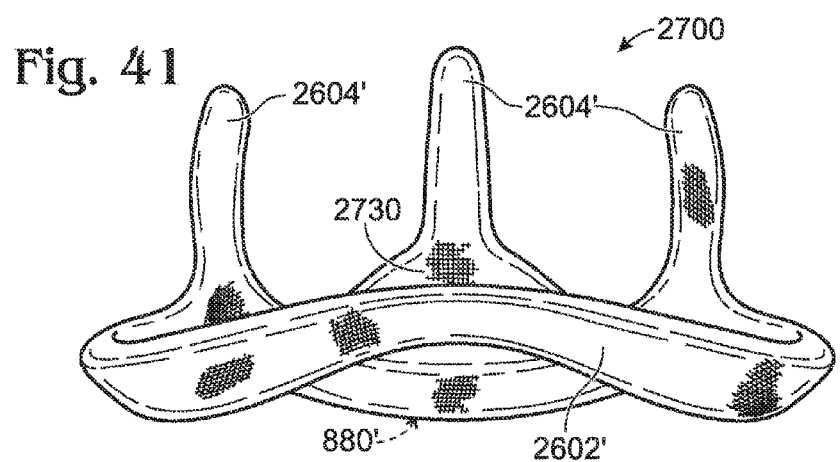
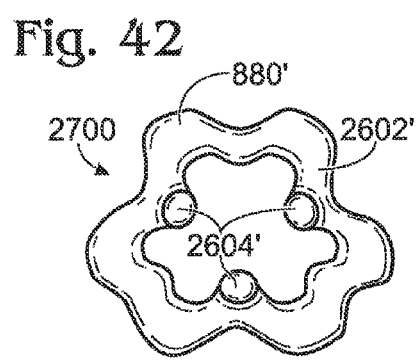

PROSTHETIC HEART VALVE FRAME WITH FLEXIBLE COMMISSURES

CROSS REFERENCE TO RELATED APPLICATION

The present application claims the benefit of and priority to provisional application Ser. No. 61/386,833, filed Sep. 27, 2010, and provisional application Ser. No. 61/472,083, filed Apr. 5, 2011, both of which are incorporated by reference herein in their entirety.

FIELD

The present application concerns implantable prosthetic valves and valve frames, and related methods and systems, such as for example, prosthetic aortic valves that can be implanted using minimally invasive surgical techniques.

BACKGROUND

In vertebrate animals, the heart is a hollow muscular organ having four pumping chambers as seen in FIG. 1: the left and right atria and the left and right ventricles, each provided with its own one-way valve. The natural heart valves are identified as the aortic, mitral (or bicuspid), tricuspid, and pulmonary, and are each mounted in an annulus comprising dense fibrous rings attached either directly or indirectly to the atrial and ventricular muscle fibers. Each annulus defines a flow orifice.

The atria are the blood-receiving chambers, which pump blood into the ventricles. The ventricles are the blood-discharging chambers. A wall composed of fibrous and muscular parts, called the interatrial septum separates the right and left atriums (see FIGS. 2, 3 and 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendinae from more than one papillary muscle, as seen in FIG. 1. In a healthy heart, these muscles and their tendinous chords support the mitral and tricuspid valves, allowing the leaflets to resist the high pressure developed during contractions (pumping) of the left and right ventricles.

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet coapt and form a seal, closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle. The remaining cardiac valves operate in a similar fashion.

Various surgical techniques may be used to repair a diseased or damaged valve. In a valve replacement operation, the damaged leaflets are typically excised and the annulus sculpted to receive a prosthetic valve. Due to aortic stenosis and other heart valve diseases, thousands of patients undergo surgery each year wherein the defective native heart valve is replaced by a prosthetic valve (either bioprosthetic or mechanical). Another, less drastic, method for treating defective valves is through repair or reconstruction, which is typically used on minimally calcified valves. One problem with surgical therapy is the significant insult it imposes on chronically ill patients and the associated high morbidity and mortality rates associated with surgical repair.

When a valve is replaced, surgical implantation of the prosthetic valve has typically required an open-chest surgery, during which the heart is stopped and the patient is placed on cardiopulmonary bypass (a so-called "heart-lung machine"). In one common surgical procedure, the diseased native valve leaflets are excised and a prosthetic valve is sutured to the surrounding tissue of the valve annulus. Because of the trauma associated with the procedure and the attendant duration of extracorporeal blood circulation, mortality rates during surgery or shortly thereafter typically have been high. It is well established that risks to patients increase with the duration of extracorporeal circulation. Due to such risks, a substantial number of patients with defective valves are deemed inoperable because their condition is too frail to withstand the procedure. By some estimates, up to about 50% of patients suffering from aortic stenosis and who are older than 80 years cannot undergo surgery for aortic valve replacement using conventional open-chest surgery.

Because of drawbacks associated with conventional open-heart surgery, percutaneous and minimally-invasive surgical approaches are garnering intense attention. Minimally invasive surgical techniques have been and continue to be developed. In successfully performed minimally invasive techniques, a conventional sternotomy can be avoided. Access to the heart can be by way of upper sternotomy or thoracotomy allowing a smaller incision and typically shorter healing times, as well as less pain for the patient. Blood loss is typically lower with minimally invasive techniques, hospital stays are shorter, and there may be lower morbidity and mortality rates as compared to conventional surgical techniques.

To obtain at least some of the potential benefits of the smaller incisions required by minimally invasive surgical techniques, prosthetic valves compatible with such techniques are needed. For instance, U.S. Pat. No. 5,411,522 to Andersen et al. describes a collapsible valve percutaneously introduced in a compressed state through a catheter and expanded in the desired position by balloon inflation.

In another approach, a flexible heart valve especially suitable for implanting in the aortic annulus has been proposed in U.S. Pat. No. 6,558,418 to Carpentier, et al., and U.S. Pat. No. 6,736,845 to Marquez, et al. More particularly, Carpentier and Marquez disclose single and multi-element wireform assemblies that include flexible cusps between adjacent commissure portions extending therefrom. A suture-permeable connecting band attached to the disclosed prosthetic valve follows the shape of (i.e., is coextensive with) the underlying frame. In the Carpentier and Marquez approach, the valve is secured by attaching (e.g., suturing) the connecting band (and thereby, the entire contour of the underlying frame, including the cusp and commissure portions) to the surrounding natural tissue. Although this approach represents an advancement of surgically implantable valves, the commissure portions of the frame remain fixedly attached to, and cannot move independently of, the tissue because the sewing band is coextensive with the undulating frame. In addition, suturing the complex, undulating periphery of the sewing band can be difficult and time consuming, as various parts of the valve can interfere with access to the sewing band. Although the valves disclosed in the '418 and '845 patents could be collapsed and inserted through a small incision, such as a thoracotomy, it would be difficult to suture them to the native annulus through such a small incision due to the configuration of the sewing band.

Conventional surgical valves have long-term durability, due in part to the flexibility of the valve structure, which allows the valve to flex slightly during physiologic loading. However, these surgical valves disadvantageously cannot be radially collapsed any appreciable amount, and therefore are not suitable for minimally invasive surgery procedures. Conventional surgical valves also require suturing to secure the valve to a patient's annulus. Such suturing can be disadvantageous in that it is time consuming and difficult, thus extending the length of surgery.

One heart valve designed to provide a faster method of securing the prosthetic valve to a patient's annulus is disclosed in U.S. patent application Ser. No. 12/716,961, which is incorporated herein by reference. The heart valve disclosed in the '961 application includes two separate components: a base stent and a valve component that is mounted to the base stent after the base stent is deployed within the native valve. The base stent is radially expandable and serves to anchor the valve to a patient's annulus. The base stent of the '961 application is designed to cooperate with a conventional leaflet wireform (e.g., a separate valve component). For example, the valve component includes a conventional, non-expandable surgical valve that is modified to include an expandable coupling stent that can be partially expanded to engage the base stent. Thus, the valve component disclosed in the '961 application is not collapsible for implantation through small surgical incisions. Further, because the heart valve disclosed in the '961 application includes two separate frames, construction can be time consuming and costly.

Other heart valves have been designed for minimally invasive surgery and/or percutaneous delivery methods. For example, U.S. Patent Application Publication No. 2010-0036484 discloses a balloon-expandable transcatheter heart valve and U.S. Patent Application Publication No. 2010-0049313 discloses a self-expandable transcatheter heart valve. Both of these heart valves are designed to be collapsed to a small profile and delivered through catheters. U.S. Patent Application Publication No. 2007-0213813, U.S. Pat. No. 7,201,772, and U.S. Patent Application Publication No. 2008-0249619 also disclose various heart valves that can be delivered via a catheter and implanted relatively quickly.

Accordingly, there remains a need for an improved prosthetic heart valve that facilitates placement through small incisions, facilitates easier implantation at the treatment site, and provides improved longevity. In addition, devices for, and associated methods of, implanting such improved prosthetic valves in a body lumen are also needed, especially a more efficient procedure that reduces the duration a patient needs extracorporeal circulation to undergo a cardiac valve replacement.

SUMMARY

Disclosed embodiments of a prosthetic heart valve can be both radially collapsible (and therefore suitable for minimally invasive surgical techniques) and provide for relatively quick implantation (e.g., without sutures or with a reduced number of sutures required for implantation). Disclosed embodiments can also exhibit flexibility in response to physiologic loading, thereby potentially increasing durability as compared to, for example, conventional transcatheter heart valves. Thus, disclosed embodiments of prosthetic heart valves can be implanted using small surgical incisions (e.g., via a thoracotomy) and few or no sutures for anchoring to a patient's valve. Disclosed embodiments can combine the ability of surgical valves to undergo deflection or flexion during physiologic loading with the ability of transcatheter valves to be radially compressed for minimally invasive delivery methods. These and other advantages of the disclosed embodiments can result in quicker healing, less scarring, and reduced procedure times in some instances, as well as increased durability of the valve due at least partially to the valve's flexibility under physiologic loading.

For example, one specific embodiment comprises a prosthetic heart valve frame that is radially expandable from a compressed configuration to an expanded configuration. The prosthetic valve frame can comprise a stent portion adapted to anchor against a heart valve annulus, the stent portion defining a lumen therethrough, and a wireform portion adapted to support at least one valve leaflet. In some embodiments, when the prosthetic valve frame is in the compressed configuration, at least a portion of the wireform portion is positioned within the lumen defined by the stent portion and wherein at least a part of the wireform portion is configured to undergo flexion during pulsatile-loading.

In some embodiments, the wireform portion can comprise a plurality of cusps (e.g., three cusps) each configured to engage with a respective valve leaflet. Each of the cusps can comprise a thinned portion configured to facilitate compression of the wireform portion. For example, each of thinned portions of the cusps can provide a point of least resistance to bending, thereby facilitating collapse or compression of the valve as a whole, and specifically of the wireform portion.

In some embodiments, at least a portion of the cusps can be positioned inside the lumen of the stent portion when the frame is in its compressed configuration. The cusps can be spaced apart from the stent portion along a longitudinal direction defined by the lumen of the stent portion in the expanded configuration. For example, as the prosthetic valve frame is transformed from the compressed configuration to the expanded configuration, at least a portion of the cusps can move from being positioned at least partially inside the lumen of the stent portion to a position longitudinally spaced from the stent portion (e.g., outside of the lumen of the stent portion). In some embodiments, the stent portion comprises a plurality of upright struts spaced around the circumference of the stent portion. The upright struts can extend to an outflow end of the wireform portion and can be configured to couple the wireform portion to the stent portion.

Adjacent cusps can be coupled to one another at each of the upright struts so as to form a commissure support at each upright strut. Some embodiments of a prosthetic valve can comprise a plurality of leaflets each having two opposing tabs, the tabs of adjacent leaflets being configured to be coupled together at a respective commissure support. For example, at least a portion of each of the leaflet tabs can be wrapped around at least a portion of an upright strut. In some embodiments, the upright struts can extend to a T-shaped termination positioned along a respective commissure support.

At least a part of the wireform portion can be configured to undergo flexion during pulsatile loading (e.g., when implanted in a patient's native valve annulus). For example, the upright struts and/or the commissure supports can be configured to flex radially inward and/or radially outward in response to blood flow through the prosthetic valve after implantation. In some embodiments, an inflow end of the stent portion can be flared outward in the expanded configuration, the inflow end being opposite the wireform portion.

The stent portion of some embodiments can comprise a circumferential strut adjacent the wireform portion. Additionally or alternatively, the stent portion can comprise a plurality of vertical struts extending from an inflow end of the stent portion toward the wireform portion. In some embodiments, the vertical struts can be spaced apart from one another, positioned between adjacent upright struts, and can terminate at the circumferential strut, if present. Disclosed embodiments can comprise a flexible skirt (e.g., a fabric skirt, such as a polyester skirt) coupled to the stent portion and configured to prevent leakage through the stent portion. A skirt can be positioned on the inside and/or outside of the stent portion lumen (e.g., one or more flexible skirts can be coupled to the inner surface of the stent portion and/or to the outer surface of the stent portion). Additionally or alternatively, the prosthetic valve can include a sealing ring coupled to the wireform portion, the sealing ring being configured to be positioned supraannularly.

In another embodiment, a radially collapsible and expandable prosthetic heart valve can comprise a frame configured to anchor the prosthetic heart valve to a patient's native valve, a leaflet-supporting structure comprising a plurality of leaflet-supporting cusps and a plurality of commissure posts, the commissure posts being positioned between adjacent leaflet-supporting cusps, wherein the commissure posts are configured to undergo cantilevered motion under physiologic loading, and a plurality of connecting segments spaced apart from one another, each connecting segment extending from a first end of the stent portion adjacent the leaflet-supporting structure to a leaflet-supporting cusp.

The frame and the leaflet-supporting structure can be undetachably coupled to one another to form a one-piece prosthetic heart valve. The leaflet-supporting structure can comprise a cloth covering surrounding the leaflet-supporting cusps and the commissure posts. The prosthetic heart valve can also be provided with a plurality of leaflets, each leaflet being coupled to a respective leaflet-supporting cusp by suturing to the cloth covering. The leaflets can be configured such that a central hole through the leaflets remains open when the prosthetic heart valve is at rest. The radially collapsible and expandable prosthetic heart valve can also include a sealing ring coupled to the leaflet-supporting structure, the sealing ring being configured to be positioned supraannularly.

Other embodiments of a prosthetic heart valve that is radially expandable from compressed configuration to an expanded configuration can comprise a plastically expandable (e.g., balloon-expandable) stent portion configured to anchor the prosthetic valve against a heart valve annulus and a self-expandable wireform portion that is separate from the stent portion. The stent portion can define a lumen therethrough, and the stent portion can be radially expandable from a collapsed state to an expanded state. In some embodiments, the stent portion can be a pre-crimped stent portion that is expandable from a pre-crimped state to an inflated state. In some embodiments, the wireform portion and the stent portion are coupled together only by one or more non-metallic components or devices. In one example, both the wireform portion and the stent portion can be coupled to a cloth-covered leaflet support stent, which effectively couples the wireform portion to the stent portion.

The self-expandable wireform portion can comprise at least one commissure support and at least one cusp adapted to support at least one valve leaflet, and the wireform portion can be radially expandable from a constrained configuration to a stress-free configuration. In some embodiments, the stiffness of the stent portion in its collapsed state is sufficient to prevent the wireform portion from expanding to its stress-free configuration. In some embodiments, the stent portion comprises stainless steel, cobalt chromium, or alloys or combinations thereof, and the wireform portion comprises Nitinol, NiTiCr, NiTiCo, or alloys or combinations thereof.

Some embodiments of a prosthetic heart valve can include a flexible leaflet support stent coupled to the wireform portion, and/or a sealing ring coupled to the flexible leaflet support stent and to the stent portion, wherein the sealing ring is configured to be positioned supraannularly.

In some embodiments, at least one valve leaflet can be at least partially wrapped around a respective post of a flexible leaflet support stent and the sealing ring can be sutured to a plurality of circular openings on the stent portion. In some embodiments, the leaflets can each have two opposing tabs, where the tabs of adjacent leaflets are configured to be coupled together at a respective commissure support. For example, at least a portion of each of the leaflet tabs can be wrapped around a post of a flexible leaflet support stent. In some embodiments, the wireform portion comprises three cusps configured to engage with a respective valve leaflet, and each of the cusps comprises a thinned portion configured to facilitate compression of the wireform portion.

Methods of making and using a prosthetic heart valve are also disclosed. For example, one method of implanting a prosthetic heart valve comprises radially compressing a prosthetic heart valve to a compressed configuration, wherein the prosthetic heart valve comprises a stent portion configured to anchor the prosthetic heart valve to a patient's native valve and a leaflet-supporting structure, delivering the compressed prosthetic heart valve to or near a patient's native valve annulus, positioning the leaflet-supporting structure of the prosthetic heart valve supraannularly to a patient's aortic valve, and expanding the prosthetic heart valve to an expanded configuration, wherein the diameter of the prosthetic heart valve in the expanded configuration is greater than the diameter of the prosthetic heart valve in the compressed configuration, and wherein in the compressed configuration at least a portion of the leaflet-supporting structure is positioned within a lumen of the stent portion, and in the expanded configuration the leaflet-supporting structure is positioned externally to the lumen of the stent portion.

In some methods, the prosthetic heart valve includes a one-piece prosthetic heart valve frame. In some methods, delivering the prosthetic heart valve can comprise delivering the prosthetic heart valve transapically. In some methods, expanding the prosthetic heart valve can effectively anchor the prosthetic heart valve without suturing the valve to the native valve.

In other methods, a pre-crimped balloon expandable stent portion can be provided and configured to anchor the prosthetic heart valve to a patient's native valve. The pre-crimped stent portion can be coupled to a self-expanding wireform portion and a plurality of leaflets to form the prosthetic heart valve, and the stent portion and the wireform portion can be coupled to one another via a cloth-covered flexible leaflet support stent. In some methods, the diameter of the stent portion in an expanded configuration is greater than the diameter of the stent portion in a compressed configuration, and expansion of the stent portion can enable self-expansion of the wireform portion.

The foregoing and other objects, features, and advantages of the invention will become more apparent from the following detailed description, which proceeds with reference to the accompanying figures.

BRIEF DESCRIPTION OF THE DRAWINGS

FIG. 1 illustrates an anatomic anterior view of a human heart, with portions broken away and in section to view the interior heart chambers and adjacent structures.

FIG. 2 illustrates an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.

FIG. 3 shows an anatomic superior view of a section of the human heart shown in FIG. 2, with the tricuspid and mitral valves closed and the aortic and pulmonary valves open during ventricular systole (ventricular emptying) of the cardiac cycle.

FIG. 4 shows an anatomic anterior perspective view of the left and right atria, with portions broken away and in section to show the interior of the heart chambers and associated structures, such as the fossa ovalis, coronary sinus and the great cardiac vein.

FIG. 7 shows an elevation view of one embodiment of a one piece prosthetic heart valve frame in an expanded configuration.

FIG. 8 shows a perspective view of the prosthetic heart valve frame of FIG. 7.

FIG. 10 is a perspective view of the prosthetic heart valve frame of FIGS. 7-8 in a collapsed configuration.

FIG. 11 is an elevation view of another embodiment of a one piece prosthetic heart valve frame in an expanded configuration.

FIG. 12 is a top plan view of the prosthetic valve frame of FIG. 11 in an expanded configuration.

FIG. 13 is a top plan view of the collapsed prosthetic heart valve frame of FIGS. 11-12.

FIG. 14 shows an elevation view of the prosthetic heart valve frame of FIGS. 11-13 in a collapsed configuration.

FIG. 15 is a section view of one method of leaflet attachment, taken along line 12-12 in FIG. 11.

FIG. 16 is a section view of an alternative method of leaflet attachment.

FIG. 40 shows a perspective view of another embodiment of a leaflet support stent for use with the disclosed prosthetic heart valve frame.

FIG. 41 shows a side elevation view of the leaflet support stent shown in FIG. 40, combined with a sealing ring and having a cloth covering surrounding it.

FIG. 42 shows a top plan view of the cloth-covered leaflet support stent of FIG. 41, in a radially compressed configuration.

DETAILED DESCRIPTION

Figure 5:
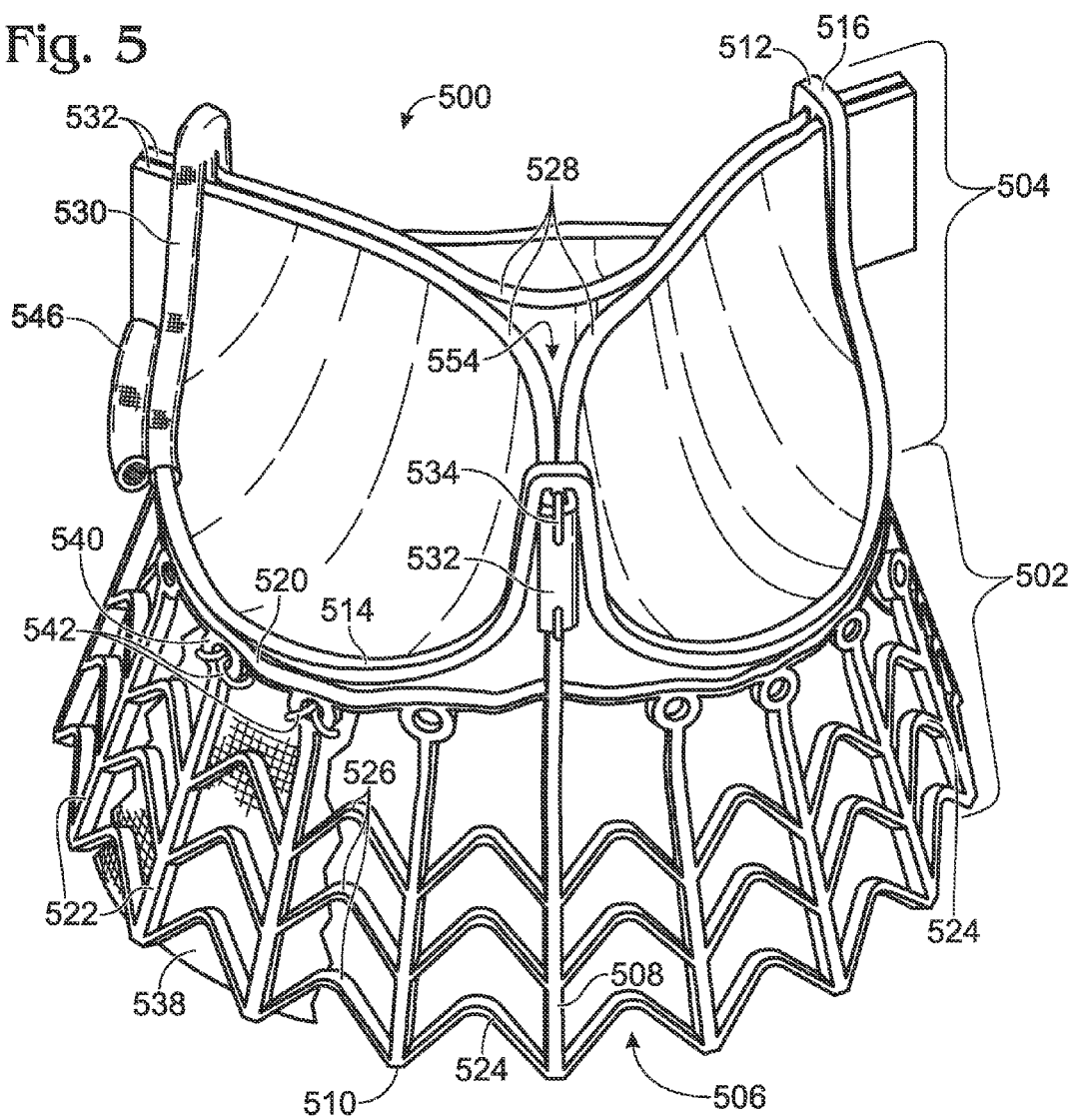
FIG. 5 shows a perspective view of one embodiment of a one piece prosthetic heart valve frame with leaflets partially secured to the frame.

As used in this application and in the claims, the singular forms "a," "an," and "the" include the plural forms unless the context clearly dictates otherwise. Additionally, the term "includes" means "comprises." Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

As used herein, "self expand" means to elastically recover from a collapsed (e.g., a compressed) configuration when an external restraint (e.g., a suture, a sheath, or a holder) is removed. A component also self-expands if it expands upon exposure to a threshold temperature inside the body. Additionally, a component self-expands if it elastically recovers from a collapsed state in response to expansion of another component. For example, as will be described below, in some embodiments, the wireform portion can self-expand after balloon expansion of the stent portion, where the stent portion is stiff enough to hold the wireform portion in its collapsed state, preventing self-expansion of the wireform portion while the stent portion is in its compressed configuration.

As used herein, "balloon expandable" means to plastically expand from a collapsed state with the use of an inflatable or expandable device, such as an inflatable balloon positioned on a delivery catheter.

As used herein, "at rest" means a configuration of a valve and/or a frame when the respective valve and/or frame is still and free from externally applied loads (e.g., pressure gradients through the valve, forces applied by retaining and/or delivery devices to retain the valve in a collapsed configuration).

As used herein, a structure is "undetachably coupled" to another structure if the structures cannot be separated from one another without destroying or otherwise rendering inoperable the device (e.g., the structures cannot be separated from one another without cutting through metal).

As used herein, the term "wireform" refers generally to a portion of a prosthetic heart valve that supports the leaflets. A wireform may or may not be formed from one or more pieces of wire. A wireform includes a three-dimensional body formed of one or more wires or similarly-shaped elongate members. A wireform as used herein can also be cut or otherwise formed from tubing or a sheet of material. In some embodiments, each of the one or more members has a substantially constant cross-sectional shape along its length. In some embodiments, one or more of the elongate members forming the wireform can have portions of varying cross-sectional shape or thickness along its length. By way of example, elongate members can have a substantially solid, rectangular or square cross-sectional shape. Other cross-sectional shapes (e.g., circular, annular, hollow rectangle) are also possible.

Overview

Disclosed embodiments of a prosthetic heart valve can advantageously provide a heart valve that allows for flexion (e.g., slight movement) during in vivo pulsatile loading as well as the capability to be radially compressed or collapsed for delivery, such as delivery via minimally invasive surgical techniques, and expanded. While the described embodiments relate to heart valve prostheses, disclosed concepts can also be applied to other types of valves as well.

Generally, disclosed embodiments of prosthetic heart valve frames can be categorized as being one-piece frames or two-piece frames. FIGS. 5-18 illustrate prosthetic valves and valve components utilizing one-piece frames. FIGS. 19-42 illustrate prosthetic valves and valve components utilizing two-piece frames. For convenience and clarity, the one-piece valve frames will be discussed first, followed by the two-piece valve frames, but this organization does not in any way limit the scope of disclosed prosthetic heart valves. Variations and components discussed with respect to one frame type can also be applied to the other frame type in some embodiments, and the disclosure should not be read to be otherwise limiting.

Overview of Prosthetic Valve Having a One-Piece Valve Frame

FIG. 5 shows a prosthetic heart valve 500, which generally includes a stent portion 502 and a wireform portion 504. The stent portion 502 can be formed of a plurality of vertical and horizontally-extending struts 522, 524, and the wireform portion 504 can include leaflet-supporting cusps 514 and commissure supports 516. Upright struts 508 (also referred to as commissure posts) can undetachably couple the stent portion 502 to the wireform portion 504. The prosthetic valve 500, which is shown in an expanded configuration in FIG. 5, can also include a plurality of leaflets 528, a flexible skirt 538 (shown partially broken away), a sealing ring 546 (shown partially broken away), and a cloth covering 530 (shown partially broken away) over the wireform portion 504, each of which will be described in further detail below.

Figure 6:
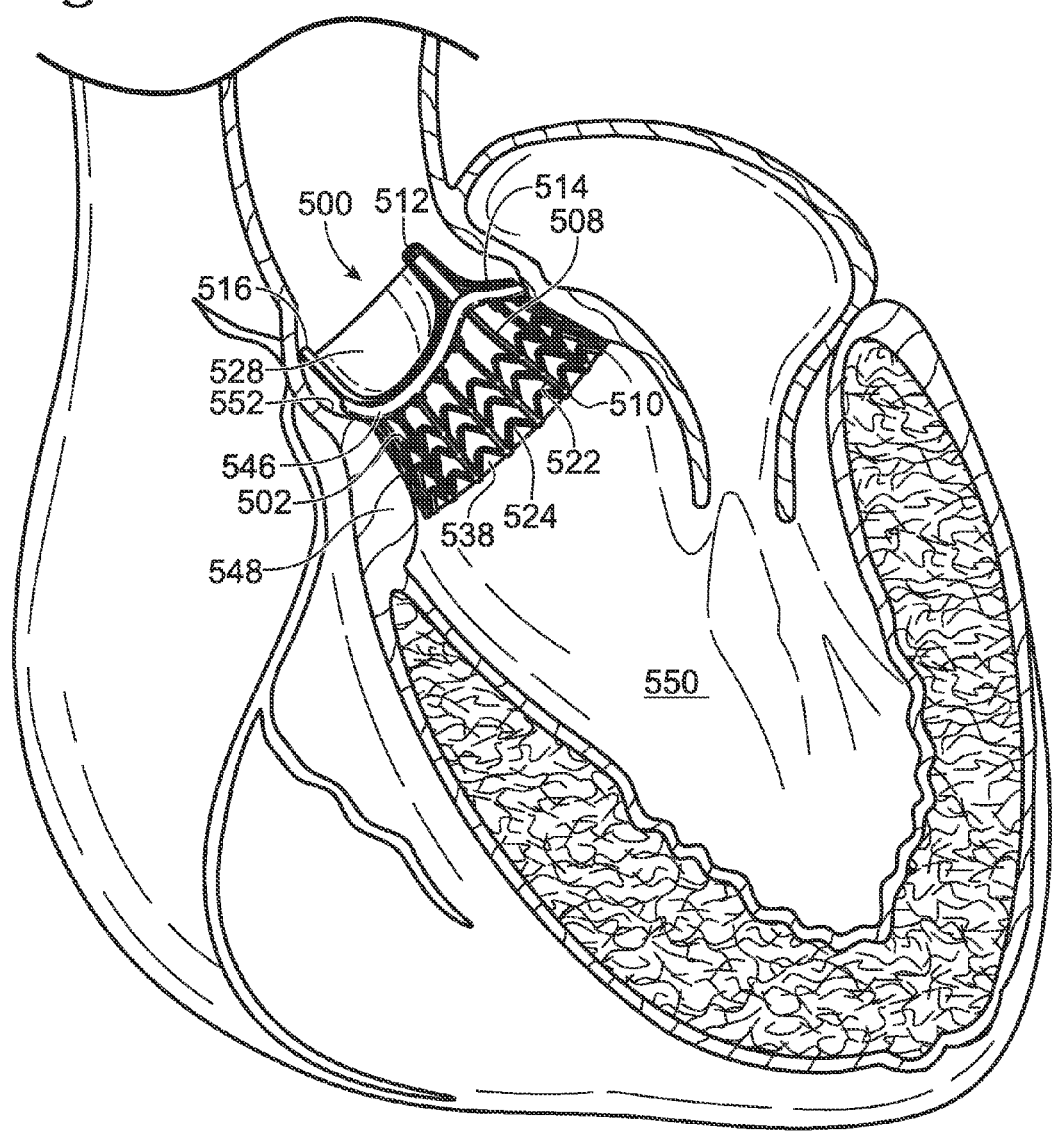
FIG. 6 shows a cutaway view of a human heart with a prosthetic heart valve implanted within the native valve annulus.

FIG. 6 shows the prosthetic heart valve 500 implanted within a patient's native valve annulus 548 (e.g., aortic valve annulus 548). As shown, the prosthetic valve 500 can be implanted such that at least a portion of the valve 500 is positioned supraannularly. For example, the wireform portion 504 can be positioned supraannularly, while the stent portion 502 is configured to anchor the prosthetic valve 500 in place within the native valve annulus 548. The stent portion 502 can be slightly flared outward at the inflow end 510, such that the stent portion 502 frictionally engages the native valve annulus 548 to prevent migration of the prosthetic valve 500. Additionally or alternatively, an optional sealing ring 546 can be provided adjacent the wireform portion 504. Said sealing ring can be configured to engage the shelf 552 of the native valve annulus 548 so as to prevent migration of the prosthetic valve 500 into the ventricle 550. The sealing ring 546 can also create a seal around the prosthetic valve 500 such that substantially no blood can pass between the native valve annulus 548 and the prosthetic valve 500.

Thus, disclosed embodiments can be positioned supraannularly to a patient's native valve (e.g., the stent portion can be positioned at least partially within the annulus and at least part of the wireform portion can be positioned supraannularly). In this position, a prosthetic valve may experience significant pressure during diastole, which can push the prosthetic valve down towards the ventricle. The cusps of the wireform portion can be configured to engage with the annulus, creating a shelf to resist such pressure (e.g., the cusps of the wireform portion can have a greater diameter than the native annulus). Additionally or alternatively, the optional flexible sealing ring can be configured to rest on the native annulus when the prosthetic heart valve is deployed in place at the target site. For example, the sealing ring can have a greater diameter than the native annulus and can thereby further resist movement or dislodgement of the valve towards the ventricle.

Components of the prosthetic valve 500 will now be described in greater detail.

Leaflets

Returning to FIG. 5, the wireform portion 504 can comprise a plurality of cusps 514 configured to engage with a respective valve leaflet 528. For example, prosthetic valve 500 includes three cusps 514, each of the cusps 514 being configured to engage with one of three leaflets 528 secured to prosthetic valve 500. For example, leaflets can be secured to the cusps 514 in a manner similar to conventional surgical valves, with the leaflets being sutured to the cloth covering 530 surrounding the cusps 514. In this manner, the leaflets 528 can open when exposed to a positive pressure gradient in a fluid (e.g., blood) passing between the inflow end 510 and the outflow end 512 and close (or coapt) when exposed to a negative pressure gradient between the inflow end 510 and the outflow end 512. When the leaflets 528 are closed, as shown in FIG. 5, they can be configured to retain a central hole 554 through the center of the leaflets 528 when the valve 500 is at rest (e.g., not subject to any pressure gradient). When the leaflets 528 are subjected to a pressure gradient (e.g., after implantation in a patient's native valve annulus) the leaflets can be configured to close completely such that substantially no blood leaks through the closed leaflets during diastole. Conventional prosthetic valves configured to be radially compressed for delivery disadvantageously must be configured such that the leaflets close completely when the valve is at rest.

For illustration purposes, the leaflets 528 are shown with coupling to the prosthetic valve 500 still in progress. The leaflets 528 can each include tabs 532 at opposing ends of the leaflets. The tabs 532 can facilitate coupling of the leaflets 528 to the wireform portion 504. For example, as will be explained in further detail below in connection with FIGS. 15-16, each tab 532 can extend between an upright strut 508 and an extension of one of the leaflet-supporting cusps 514 adjacent the outflow end 512 (e.g., adjacent the commissure support 516). Adjacent tabs 532 can be at least partially wrapped around the respective upright strut 508 and coupled together (e.g., with sutures 534) around the upright strut 508. In FIG. 5, only one of the three sets of leaflet tabs 532 has been sutured together around an upright strut 508. The leaflets can additionally be secured to the frame such as by being sutured to the cloth covering 530 surrounding the cusps 514.

Examples of suitable materials for forming the valve leaflets include pericardial tissue (e.g., bovine, porcine, or cadaver pericardial tissue), biocompatible synthetic polymers, and any other suitable natural or synthetic material. While three leaflets are shown, various embodiments can comprise one, two, three, or more leaflets.

Flexible Skirt

In addition to leaflets, the prosthetic valve 500 can include a flexible skirt 538. The flexible skirt 538 can be, for example, a polyester fabric (e.g., Dacron) skirt. The flexible skirt 538 is shown coupled to the inner surface of the stent portion 502 (e.g., positioned within a lumen 506 of the stent portion 502) and can be configured to prevent leakage through the stent portion 502 once the prosthetic valve 500 is implanted within a patient's native valve. In the specific embodiment shown, the flexible skirt 538 can be coupled to one or more of the vertical struts 522, such as to circular portions 540 adjacent the circumferential strut 520 (e.g., with sutures 542). In other embodiments, skirt 538 can be coupled to the stent portion 502 in additional places and/or in alternative arrangements.

While FIG. 5 shows the skirt 538 positioned within the lumen 506 of the prosthetic valve 500, in some embodiments, skirt 538 can be positioned on the outer surface of the stent portion (e.g., outside of the lumen 506). In some embodiments, the prosthetic valve 500 can include a skirt on both the inside and outside surfaces of the stent portion 502. In alternative embodiments, the prosthetic valve can be provided without a flexible skirt 538.

While FIG. 5 shows only a cut-away view of the skirt 538, the skirt 538 can extend around the entire circumference of the stent portion 502. Additionally, as shown, the skirt 538 can be essentially the same height as the stent portion 502. For example, the skirt 538 can extend substantially from an inflow end 510 and towards an outflow end 512, terminating, in some embodiments, at cusp portions 514, or alternatively, adjacent a circumferential strut 520 positioned near the wireform portion 504. Thus, the skirt 538 can substantially cover the entire stent portion 502 and optionally the area of the wireform portion below the cusp portions 514. In alternative embodiments, the skirt 538 can be configured to only cover a portion of the stent portion 502.

Cloth Covering

The cloth covering 530 can be secured to the wireform portion 504 such that opposing longitudinal edges of the cloth 530 are brought together to form a seam external to the wireform portion 504 (see seam 1150 in FIG. 11). The seam can be formed such as by suturing, adhesion, and/or other well-known cloth-edge joining techniques. The cloth covering 530 can function to provide a substrate for suturing the leaflets to. For example, the cloth covering 530 can be sutured around the wireform portion 504 and the leaflets subsequently can be sutured to the cloth 530 along the contour of the leaflet-supporting cusps 514 (e.g., on the outside of the leaflet-supporting cusps 514). The cloth 530 can also prevent the leaflets from contacting the metal of the leaflet-supporting cusps 514 and commissure supports 516, thereby potentially decreasing wear on the leaflets. Cloth covering 530 can comprise any suitable biocompatible material, such as polyester or polyethylene terephthalate.

In some embodiments, the flexible skirt 538 can extend up to meet the cloth covering 530 on the wireform portion 504 so that there is no gap between them. The flexible skirt 538 can be coupled to the cloth covering 530 so as to not impede movement of the leaflets 528 or cusps 514. For example, as will be described in further detail below, as the prosthetic valve 500 is compressed for delivery, in some embodiments the cusps 514 move from their position in the expanded configuration to a position inside the lumen 506. The flexible skirt 538 can be coupled to the stent portion 502, the circumferential strut 520, and/or the cloth covering 530 on the wireform portion 504 so as not to impede such movement of the cusps 514. In some embodiments, the flexible skirt 538 can follow the contour of the commissure supports 516 such that everything below the leaflets 528 is substantially sealed off.

Sealing Ring

The prosthetic heart valve 500 can include a flexible sewing ring or sealing ring structure, such as a tri-lobular sealing ring. The sealing ring can be arranged such that sinus-shaped portions of the ring can be aligned with the cusps of the wireform portion. The sealing ring can form a tight seal between the wireform portion and the stent portion of disclosed prosthetic heart valve frames, can form a tight seal between the prosthetic valve and native valve annulus, and/or can provide a suture point for securing the prosthetic valve frame to the native valve annulus (in addition to or instead of using the flared stent portion to anchor the valve frame). For example, a flexible sealing ring 546 can be coupled to the wireform portion 504 in some embodiments and can be used to attach nadir sutures to the patient's annulus. In other embodiments, the sealing ring 546 can be provided without suturing it to the native valve tissue. The sealing ring 546 can additionally or alternatively be configured to provide a seal positioned between the wireform portion 504 and the stent portion 502 of the prosthetic heart valve frame, the seal being configured to enhance the effectiveness of or replace the flexible skirt discussed above.

The sealing ring 546 can be sewn to the wireform cloth 530 through the leaflets in some embodiments. In some embodiments, the leaflets can be sandwiched between the wireform cloth 530 and the sealing ring 546, which may or may not include a cloth covering itself. FIG. 5 shows that the sealing ring 546 can be positioned on the wireform portion 504 adjacent the stent portion 502.

Frame Structure

Embodiments of a frame for use with a prosthetic heart valve will now be described. FIGS. 7-8 illustrate the frame 501 of the prosthetic heart valve 500 of FIG. 5, with the frame still in its expanded configuration. The frame 501 is shown without a plurality of leaflets, a cloth covering over a portion of the frame, a sealing ring, or a fabric or flexible skirt of another material, in order to provide a clear view of the frame.

Frame 501 can comprise a stent portion 502 and a wireform portion 504 (wireform portion 504 is also referred to as a leaflet support portion). Generally, stent portion 502 can be configured to anchor the frame 501 to a patient's native valve annulus and wireform portion 504 can be configured to receive and support at least one valve leaflet. For example, once the prosthetic valve 500 is positioned at an implantation site, the stent portion 502 can engage an inner periphery of a body lumen (e.g., a native annulus) at the implantation site. Disclosed embodiments can engage with the native annulus via the stent portion 502 and/or a sealing ring, such as by engaging the aortic annulus, the fibrous annulus, and/or the aorta wall (e.g., a position downstream from the location of the native leaflets)

The stent portion 502 can define a lumen 506 therethrough. The stent portion 502 can comprise any suitable combination of struts and wires that can allow the stent portion to radially collapse to a compressed configuration for delivery, and that can also facilitate anchoring of the frame 501 within a patient's native valve.

The specific embodiment shown in FIGS. 7-8 includes a plurality of upright struts 508 spaced around the circumference of the stent portion 502. The upright struts 508 can extend substantially from an inflow end 510 to an outflow end 512 of the frame 501. As shown in FIGS. 7-8, the inflow end 510 corresponds to the end 510 of the stent portion 502 opposite the wireform portion 504. In alternative embodiments, the upright struts may extend only partially towards the inflow end 510 and/or only partially towards the outflow end 512. The upright struts 508 can be configured to couple the stent portion 502 to the wireform portion 504. For example, the upright struts can undetachably couple the stent portion 502 and the wireform portion 504 so that the frame 501 is a one-piece frame 501.

In some specific embodiments, each of the cusps 514 can include a thinned portion 515 (best seen in FIG. 7) configured to facilitate compression of the wireform portion 504. The upright struts 508 can, in some embodiments, carry at least a portion of the load due to pulsatile loading, and can therefore at least partially reduce the load on the cusps 514. Thus, the upright struts 508 can at least partially compensate for any reduction in strength of the cusps 514 due to the thinned portion 515.

The one or more thinned portions 515 can be configured to provide the cusps 514 with greater flexibility, especially near the thinned portions 515. For example, the thinned portion 515 can be configured to deform more readily than the adjacent, thicker, areas of the cusps 514. In some embodiments, the thinned portions 515 can be positioned substantially near the center of each cusp, but other configurations are also suitable. For example, each cusp 514 could include at least two thinned portions 515 spaced apart from each other along the cusp 514. The thinned portions 515 can, for example, serve as a hinge and facilitate bending of the cusps 514 during transformation of the wireform portion 504 (and the frame 501 as a whole) from the expanded configuration shown in FIGS. 7-8 to a compressed configuration.

As shown in FIG. 7, in an expanded configuration, the cusps 514 can be spaced apart from the stent portion 502 along a longitudinal direction defined by the lumen 506 of the stent portion 502. For example, the cusps 514 can be spaced apart from the stent portion 502 along the longitudinal axis Z in the shown expanded configuration. Additionally or alternatively, the cusps 514 can be positioned further outward radially than the stent portion 502 when in the expanded configuration. For example, the cusps 514 can have a greater diameter in the expanded configuration than the circumferential strut 520. In this configuration, the cusps 514 can engage the native valve annulus (e.g., the shelf 552 of annulus 548 seen in FIG. 6).

Adjacent cusps 514 can be coupled to one another at each of the upright struts 508 so as to form a commissure support 516 at each upright strut 508 adjacent the outflow end 512. For example, with reference to FIG. 8, adjacent cusps 514a and 514b can be coupled to one another at upright strut 508a to form a commissure support 516a. Similarly, adjacent cusps 514a and 514c can be coupled to one another at upright strut 508b to form commissure support 516b, and adjacent cusps 514b and 514c can be coupled to one another at upright strut 508c to form commissure support 516c.

The commissure supports 516 can lean slightly outward relative to the lumen 506 (e.g., the central flow axis Z of the prosthetic valve frame 501) when the valve is at rest. The commissure supports 516 can alternatively be oriented to lean inwardly at a slight angle relative to the longitudinal axis Z. Alternatively, the commissure supports 516 can be substantially vertical (e.g., substantially parallel to the central flow axis) when the valve is at rest, as shown in FIG. 7.

At least part of the wireform portion 504 can be configured to undergo flexion (e.g., can be configured to move slightly) during normal physiologic loading when implanted in a patient's native valve. For example, the upright struts 508 and commissure supports 516 (e.g., the free end of the commissure supports 516 adjacent the outflow end 512) can be configured to flex in the direction indicated by arrows 518 (e.g., radially inward) during each cardiac cycle, and likewise can be configured to move radially outward, returning to their original positions later in each cardiac cycle.

The prosthetic valve frame 501 can be positioned at the implantation site such that the cantilevered commissure supports 516 can deflect independently of the surrounding body lumen to which the valve frame 501 is secured. The ability of the commissure supports 516 to flex in this manner can allow the leaflets supported by the commissure supports 516 and cusps 514 to close more gently, thereby relieving stress on the leaflets during diastole.

In some embodiments, the wireform portion 504 and/or the upright struts 508 can be thinner than would normally be expected, in order to optimize the movement (e.g., flexion) during pulsatile in vivo loading. Such flexion can contribute to the longevity and durability of disclosed prosthetic heart valve frames 500. The stiffness of the upright struts 508 and/or the wireform portion 504 can be optimized such that the commissure supports 516 deflect under physiologic loading.

In some embodiments, the upright struts 508 and/or commissure supports 516 can be configured to deflect an amount similar to that of conventional surgical valves and an amount greater than that of conventional transcatheter valves. For example, while a conventional transcatheter valve may only flex tens of microns or less, the presently disclosed valve frames can flex up to around 1 mm or more, with flexion varying slightly with different sized valve frames. Thus, the presently disclosed prosthetic heart valve frames can flex about 10-100 times more than conventional transcatheter valves.

Figure 9:
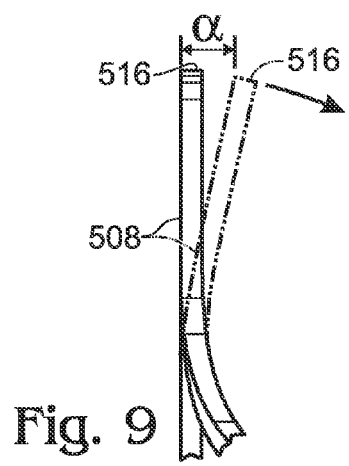
FIG. 9 shows a close-up of a portion of the prosthetic heart valve frame of FIG. 7.

For example, FIG. 9 shows the deflection of a commissure support 516 under physiologic loading. The commissure support 516 and upright struts 508 can move in a cantilevered fashion radially inward and outward during each cardiac cycle. As shown in FIG. 9, the commissure support 516 can deflect radially inward a distance $\alpha$. In some embodiments, $\alpha$ can be about 1 mm or greater.

Such flexion can be adjusted and optimized to improve hemodynamics through the valve. For example, as a result of this greater flexion, the leaflets can advantageously be arranged to retain a central hole (e.g., the three-pointed star-shaped hole 554 seen in FIG. 5 where the leaflets meet in the center of the valve) when the valve is at rest (i.e., not subjected to any pressure gradient). Under physiologic loading (and flexion of the commissures), the central hole is closed completely, but the leaflets generally come together in a controlled, gentle fashion. On the other hand, conventional transcatheter valves typically cannot have such a central hole in the leaflets—the leaflets must be completely closed when the valve is at rest, because the valve is unable to flex. As a result, the leaflets of traditional transcatheter valves tend to collide together more forcefully, which can disadvantageously reduce the lifespan of the prosthetic valve.

Returning to FIGS. 7-8, the stent portion 502 of the frame 501 can be flared outward in its expanded configuration. For example, the diameter of the lumen 506 at the inflow end 510 of the stent portion 502 can be greater than the diameter of the lumen 506 of the stent portion 502 adjacent the wireform portion 504, thereby creating a flared stent portion 502. The flared configuration of the stent portion 502 can facilitate anchoring of the stent portion 502 within the patient's native valve annulus without the use of sutures (or with a reduced number of sutures as compared with conventional prosthetic heart valves). For example, as shown in FIG. 6, the flared stent portion 502 can engage with the valve annulus, keeping the frame 501 in position, with the wireform portion 504 being positioned distal to the annulus. Therefore, in some embodiments, at least part of the wireform portion 504 does not contact the native valve annulus once the frame 501 is implanted. For example, in some embodiments, the cusps 514 and/or a sealing ring may contact the native valve annulus, while the commissure supports 516 do not.

In some embodiments, the leaflet-supporting cusps 514 can protrude radially outward past the stent portion 502 (or at least past the upper end of stent portion 502 adjacent the cusps 514) so as to form an edge or shelf which can further discourage migration of the prosthetic heart valve frame 501 during diastole (e.g., the shelf formed by the cusps 514 could engage with or rest against the native annulus, thereby working together with the flared stent portion to prevent migration of the valve frame into the ventricle). In other words, the flared lower end of the stent portion 502 can be positioned on one side of the native annulus and can have a diameter larger than the annulus to prevent migration in one direction, while the cusps 514 can be positioned on the opposite side of the annulus and can have a diameter larger than the annulus to prevent migration in the opposite direction. For example, in embodiments where the frame 501 comprises Nitinol or another superelastic material (e.g., shape memory materials), the cusps 514 can be shape set such that they are positioned further out radially than at least the upper end of stent portion 502 in the expanded configuration.

In some embodiments, the frame 501 can include a circumferential strut 520. The circumferential strut 520 can be positioned on the stent portion 502 adjacent the wireform portion 504 and can be configured to increase the radial stiffness of the stent portion 502 and/or increase the effective stiffness of the upright struts 508. Circumferential strut 520 can be configured to be essentially straight (e.g., have an essentially flat side profile) when the frame 501 is in its expanded configuration and can be bent or folded with the frame 501 is in its compressed configuration. The circumferential strut 520 can essentially serve as a boundary between the stent portion 502 and the wireform portion 504, although the upright struts 508 continue from one side of the circumferential strut 520 to the other.

The stent portion 502 can also include a plurality of vertical struts 522 that extend from the inflow end 510 to the circumferential strut 520. The vertical struts 522 can be spaced apart from one another and a plurality of vertical struts 522 can be positioned between adjacent upright struts 508. At least one row of horizontally-extending struts 524 can be positioned around the circumference of the stent portion, extending between adjacent vertical struts 522 and/or between an upright strut 508 and a vertical strut 522. FIGS. 5-8 show three rows of horizontally extending struts 524, but more or fewer rows are also possible. In the specific embodiment shown, the horizontally-extending struts 524 can be substantially U-shaped or V-shaped, with the curved portion or vertex portion 526 arranged towards the outflow end 512 of the frame 501. Bending or extending of the horizontally-extending struts 524 can decrease or increase, respectively, the distance between adjacent vertical struts 522 or the distance between an adjacent vertical strut 522 and upright strut 508. Thus, the horizontally-extending struts 524 can facilitate compression of the stent portion 502 and therefore can facilitate compression of the overall frame 502. Other shapes and configurations of the stent portion are also possible. Generally, any shape or design can be provided as the stent portion of disclosed prosthetic heart valves that allow for radial compression and expansion of the stent portion.

FIG. 10 shows the valve frame 501 in a collapsed configuration (e.g., radially compressed for delivery). As shown in FIG. 10, when the valve frame 501 is radially compressed, the circumferential strut 520 can become pinched into a V shape between adjacent circular openings 540. As shown in FIG. 10, in the compressed configuration, at least a portion of the wireform portion 504 can be positioned at least partially inside the stent portion 502. For example, at least a portion of the cusps 514 can be positioned inside (e.g., within) the lumen 506 of stent portion 502 in the compressed configuration.

This positioning can be accomplished via movement of the cusps 514 towards the inflow end 510 as the stent portion 502 is being radially crimped. Thus, the wireform portion 504 can be configured to collapse further radially than the stent portion 502.

In an alternative embodiment, the wireform portion 504 can be configured to collapse less in the radial direction that does the stent portion 502. For example, at least a portion of the wireform portion 504 can be positioned at least partially outside the stent portion 502. For example, at least a portion of the cusps 514 can be positioned outside (e.g., against the outer surface) of stent portion 502 in the compressed configuration. This positioning can be accomplished via movement of the cusps 514 towards the inflow end 510 as the stent portion 502 is being radially crimped more than the cusps 514 (e.g., the stent portion 502 can be radially crimped to a smaller compressed diameter than the cusps 514).

FIGS. 11-14 illustrate an additional embodiment of a prosthetic heart valve frame 1100. FIGS. 11-12 show the valve frame 1100 in an expanded configuration and FIGS. 13-14 show the prosthetic heart valve frame 1100 in an compressed, or collapsed configuration 1100'. The prosthetic heart valve frame 1100 is similar to the prosthetic heart valve frame 501 of FIGS. 5-10 except that valve frame 1100 does not include a circumferential strut 520 on the stent portion. Additionally, the prosthetic valve frame 1100 does not include thinned portions on the leaflet-supporting cusps 1114 (e.g., thinned portions 515 of cusps 514). Either or both of these features can be provided with the embodiment shown in FIGS. 11-14.

Prosthetic valve frame 1100 can comprise a stent portion 1102 and a leaflet structure 1104. Leaflets are not shown in FIGS. 11-14, for clarity. Generally, stent portion 1102 can be configured to anchor the prosthetic valve frame 1100 to a patient's native valve annulus and leaflet structure 1104 can be configured to receive and support at least one valve leaflet. The prosthetic valve frame 1100 can define a lumen 1106 therethrough. The stent portion 1102 can comprise any suitable combination of struts and/or wires that can allow the stent portion 1102 to radially collapse to a compressed configuration for delivery, and that can also facilitate anchoring of the expanded prosthetic valve frame 1100 within a patient's native valve. The leaflet structure 1104 can comprise a plurality of leaflet-supporting cusps 1114 each configured to engage with a respective valve leaflet.

The specific embodiment shown in FIGS. 11-14 includes a plurality of commissure posts 1108 spaced around the circumference of the stent portion 1102 and positioned between adjacent leaflet-supporting cusps 1114. The commissure posts 1108 can extend substantially from an inflow end 1110 to an outflow end 1112 of the prosthetic valve frame 1100. As shown in FIGS. 11-14, the inflow end 1110 corresponds to the end 1110 of the stent portion 1102 opposite the leaflet structure 1104. In alternative embodiments, the commissure posts may extend only partially towards the inflow end 1110 and/or only partially towards the outflow end 1112. The commissure posts 1108 can be configured to couple the stent portion 1102 to the leaflet structure 1104. For example, the commissure posts 1108 can undetachably connect the stent portion 1102 and the leaflet structure 1104 so that the prosthetic valve frame 1100 is a one-piece prosthetic valve frame 1100.

As shown in FIGS. 13-14, in a compressed configuration, at least a portion of the leaflet structure 1104 can be positioned at least partially inside the frame 1102. For example, at least a portion of the leaflet-supporting cusps 1114 can be positioned inside (e.g., within) the lumen 1106 of frame 1102 in the compressed configuration. This positioning can be accomplished via movement of the cusps 1114 towards the inflow end 1110 as the frame 1102 is being radially crimped. Thus, the leaflet structure 1104 can be configured to collapse further radially than the frame 1102.

Alternatively, the leaflet structure 1104 can be configured to collapse less in the radial direction that does the frame 1102. For example, at least a portion of the leaflet structure 1104 can be positioned at least partially outside the frame 1102. For example, at least a portion of the cusps 1114 can be positioned outside (e.g., against the outer surface) of frame 1102 in the compressed configuration. This positioning can be accomplished via movement of the cusps 1114 towards the inflow end 1110 as the frame 1102 is being radially crimped more than the cusps 1114 (e.g., the frame 1102 can be radially crimped to a smaller compressed diameter than the cusps 1114).

At least part of the leaflet structure 1104 can be configured to undergo flexion (e.g., can be configured to move slightly) during normal physiologic loading when expanded and implanted in a patient's native valve. For example, the commissure posts 1108 and commissure supports 1116 can be configured to flex radially inward during each cardiac cycle, and likewise can be configured to flex radially outward to their original positions later in each cardiac cycle. Such flexion can contribute to the longevity and durability of disclosed prosthetic heart valves 1100.

FIGS. 11-12 show the valve frame 1100 in an expanded configuration 1100. The stent portion 1102 of the prosthetic valve frame 1100 can be flared outward in its expanded configuration, as shown in FIGS. 11-12. For example, the diameter of the lumen 1106 at the inflow end 1110 of the stent portion 1102 can be greater than the diameter of the lumen 1106 of the stent portion 1102 adjacent the leaflet structure 1104, thereby creating a flared stent portion 1102.

FIG. 12 shows the valve frame 1100' in its compressed configuration inside the expanded valve frame 1100 for reference. In some embodiments, disclosed prosthetic heart valves can be compressed or crimped to about 60% of its expanded size (e.g., the diameter of the valve in its compressed configuration can be about 60% of the diameter in the expanded configuration). In one specific embodiment, a 25 mm frame can be crimped to have an outer diameter of around 15 mm or less for delivery of the valve. Other sizes of prosthetic heart valves can be compressed similar amounts. For example, a size 19 mm valve can be compressed to about 11.5 mm or less, a 21 mm valve can be compressed to about 12.75 mm or less, a 23 mm valve can be compressed to about 14 mm or less, a size 27 mm valve can be compressed to about 16.25 mm or less, and a size 29 mm valve can be compressed to about 17.5 mm or less. In some embodiments, the prosthetic heart valve can be compressed to an even smaller diameter relative to the expanded diameter (e.g., less than 60% of the expanded diameter).

As seen in FIGS. 11-14, the stent portion 1102 can include a plurality of vertical struts 1122 that extend from the inflow end 1110 towards the outflow end 1112. The vertical struts 1122 can be spaced apart from one another and positioned between adjacent commissure posts 1108. At least one row of horizontally-extending struts 1124 can be positioned around the circumference of the stent portion 1102, extending between adjacent vertical struts 1122 and/or between a commissure post 1108 and a vertical strut 1122. FIGS. 11-12 and 14 show three rows of horizontally extending struts 1124, but more or fewer rows are also possible. In the specific embodiment shown, the horizontally-extending struts 1124 can be substantially U-shaped or V-shaped, with the curved portion or vertex portion 1126 arranged towards the outflow end 1112 of the prosthetic valve frame 1100. Bending or extending of the horizontally-extending struts 1124 can decrease or increase, respectively, the distance between adjacent vertical struts 1122 or the distance between an adjacent vertical strut 1122 and commissure post 1108. Thus, the horizontally-extending struts 1124 can facilitate compression of the stent portion 1102 and therefore can facilitate compression of the overall prosthetic valve 1100. Other shapes and configurations of the stent portion are also possible. Generally, any shape or design can be provided as the stent portion of disclosed prosthetic heart valves that allows for radial compression and expansion of the stent portion.

FIG. 11 shows a cloth covering 1130 that can be secured to the leaflet structure 1104 such that opposing longitudinal edges of the cloth 1130 are brought together to form a seam 1150 external to the leaflet structure 1104. The seam can be formed such as by suturing, adhesion, and/or other well-known cloth-edge joining techniques. The cloth covering 1130 can function to provide a substrate for suturing the leaflets to. For example, the cloth covering 1130 can be sutured around the leaflet structure 1104 and the leaflets subsequently can be sutured to the cloth 1130 along the contour of the leaflet-supporting cusps 1114 (e.g., on the outside of the leaflet-supporting cusps 1114).

A sealing ring 1146 (FIG. 11) can be sewn to the wireform cloth 1130 through the leaflets in some embodiments. In some embodiments, the leaflets can be sandwiched between the wireform cloth 1130 and the sealing ring 1146, which may or may not include a cloth covering itself. FIG. 11 shows that the sealing ring 1146 can be positioned on the leaflet structure 1104 adjacent the stent portion 1102. The sealing ring 1146 can be positioned between the leaflet structure 1104 and the stent portion 1102 of disclosed prosthetic heart valve frames, and can form a tight seal between the frame 1100 and the native valve annulus. Additionally or alternatively, the sealing ring 1146 can provide a suture point for securing the prosthetic valve frame to the native valve annulus (in addition to or instead of using the flared stent portion to anchor the valve frame). For example, a flexible sealing ring 1146 can be coupled to the leaflet structure 1104 in some embodiments and can be used to attach nadir sutures to the patient's annulus. In other embodiments, the sealing ring 1146 can be provided without suturing it to the native valve tissue. The sealing ring 1146 can additionally or alternatively be configured to provide a seal positioned between the leaflet structure 1104 and the stent portion 1102 of the prosthetic heart valve frame, the sealing ring 1146 being configured to enhance the effectiveness of or replace the flexible skirt discussed above.

As noted above, disclosed embodiments can be positioned supraannularly to a patient's native valve (e.g., the stent portion can be positioned at least partially within the annulus and at least part of the leaflet structure 1104 can be positioned supraannularly) and can be subjected to pressure pushing the prosthetic valve 1100' down towards the patient's ventricle. As noted, the cusps 1114 of the leaflet structure 1104 can be configured to engage with the annulus, creating a shelf to resist such pressure. Additionally or alternatively, the flexible sealing ring 1146 can be configured to rest on the native valve annulus when the prosthetic heart valve is deployed in place at the target site. For example, the sealing ring 1146 can have a greater diameter than the native annulus and can thereby further resist movement or dislodgement of the valve 1100' towards the ventricle.

While FIG. 11 does not show these components for clarity, the prosthetic heart valve frame 1100' can be provided with a plurality of leaflets, cloth coatings on the stent portion, an additional stent, and/or a flexible skirt coupled to the stent portion 1102 and configured to prevent leakage through the stent portion 1102.

Figure 17:
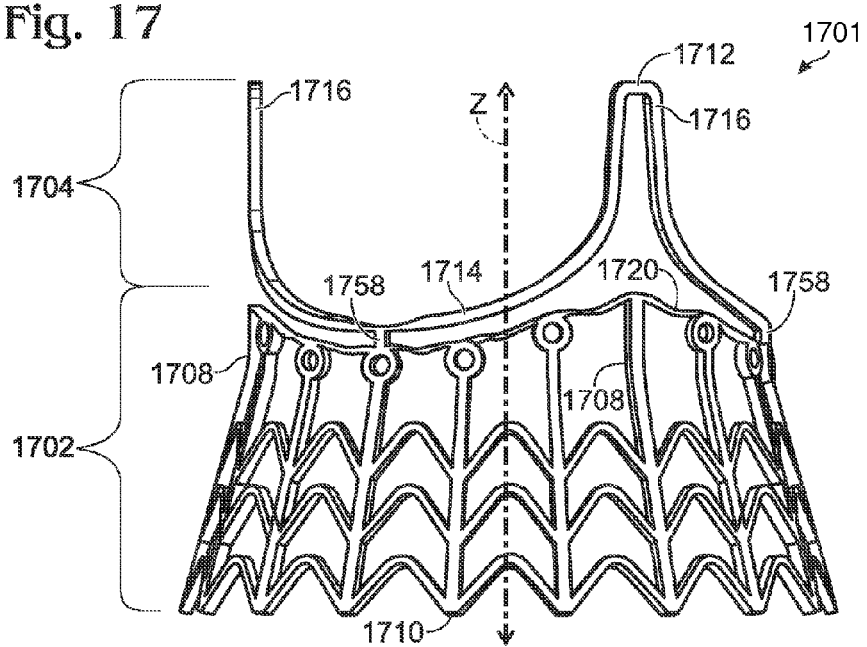
FIG. 17 is an elevation view of another embodiment of a one piece prosthetic heart valve frame.
Figure 18:
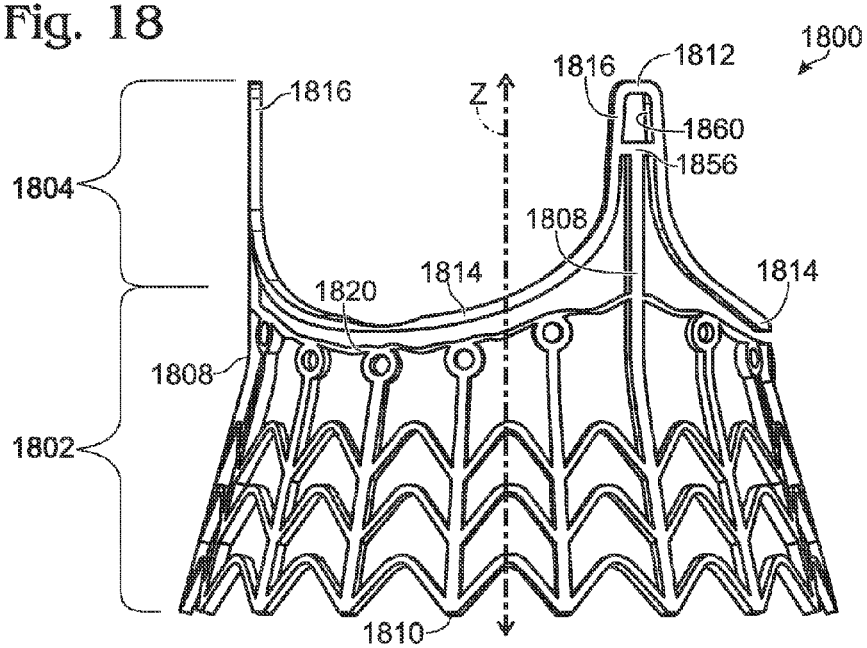
FIG. 18 is an elevation view of another embodiment of a one piece prosthetic heart valve frame.

FIGS. 17 and 18 illustrate additional embodiments of a prosthetic heart valve frame. FIG. 17 shows a prosthetic heart valve frame 1701 that is similar to the frame 501 of FIG. 7-8 except that the commissure post 1708 terminates at the circumferential strut 1720 rather than extending to the tip of the commissure support 1716 adjacent the outflow end 1712. The frame 1701 additionally includes one or more connecting segments 1758 that couple the wireform portion 1704 to the stent portion 1702. Thus, in the embodiment shown in FIGS. 7-8 the commissure posts 508 effectively couple the wireform portion 504 to the stent portion 502, but in the embodiment of FIG. 17, desirably only the connecting segments 1758 couple the wireform portion 1704 to the stent portion 1702. A connecting segment 1758 can be positioned at approximately the center of each of the cusps 1714 in some embodiments. In other embodiments, the connecting segments 1758 can be positioned at other locations along the cusps 1714. In some embodiments, each cusp may include two or more connecting segments. In some embodiments, some cusps may include connecting segments, while others do not.

The prosthetic heart valve frame 1701 can be configured to radially collapse differently than other disclosed embodiments. For example, when the frame 1701 is radially collapsed or compressed, the outflow end 1712 (e.g., the tips of the commissure supports 1716 adjacent the outflow end 1712) can move away from the stent portion 1702 along the longitudinal axis Z. By contrast, in previously disclosed embodiments, at least part of the wireform portion can be configured to move inside the lumen of the stent portion as the frame is transformed to the compressed configuration. On the other hand, frame 1701 can effectively elongate along the longitudinal axis Z as it is radially compressed so that the wireform portion 1704 resides completely outside the stent portion 1702 when both components are compressed.

FIG. 18 shows a prosthetic heart valve frame 1800 that is similar to the frame 501 of FIGS. 7-8 except with respect to the commissure posts 508, 1808, respectively. In FIGS. 7-8, the commissure post 508 extends substantially from the inflow end 510 to the outflow end 512, terminating at the outflow end 512 of the commissure support 516. By contrast, the commissure post 1808 in FIG. 18 does not extend all the way to the outflow end 1812 of the commissure support 1816. Instead, the commissure post 1808 extends only to a T-shaped termination 1856. The T-shaped termination 1856 can be positioned approximately equidistant from the circumferential strut 1820 and the outflow end 1812. In other embodiments, the T-shaped termination 1856 can be positioned higher or lower along the commissure support 1816 (e.g., closer to the outflow end 1812 as shown in FIG. 18, or closer to the circumferential strut 1820). In this embodiment, leaflet tabs can be configured to extend through the window 1860 created by the T-shaped termination. Thus, rather than wrapping leaflet tabs around the commissure post 1808, the leaflet tabs can be secured to the frame 1800 via techniques more similar to conventional surgical valves.

Disclosed embodiments of a prosthetic heart valve frame can comprise any material that allows the frame to be radially collapsible and expandable. Preferable materials allow for slight flexion of at least a portion of the frame in response to pulsatile loading. Examples of suitable materials for forming the overall frame (e.g., the stent portion and/or the wireform portion) include superelastic materials such as Nitinol or NiTiCr, as well as stainless steel, cobalt, chromium, titanium, or alloys or combinations of the same (e.g., CoCr alloys).

Some embodiments can comprise a flexible biocompatible polymer, such as polypropylene or silicon. Different frame materials can be selected depending on the method of deployment. For example, the frame can comprise a superelastic material for self-expanding embodiments, or a plastically deformable material such as CoCr for plastically expandable embodiments (e.g., embodiments that are deployed via balloon expansion).

Leaflet Attachment

FIG. 15 illustrates a section view of prosthetic heart valve frame 1100, taken along line 15-15 in FIG. 11, but with two leaflets 1528a, 1528b visible in order to illustrate one method of leaflet attachment. As shown in FIG. 15, at least a portion of upright strut 1108 and/or leaflet structure 1104 can be covered with cloth 1130. The leaflets 1528a, 1528b can be provided with tabs 1532a, 1532b on opposing ends of the leaflets 1528a, 1528b (although only one end of each leaflet 1528a, 1528b is visible in FIG. 15). Each tab 1532a, 1532b can pass between an upright strut 1108 and a portion of a leaflet structure 1104 near the outflow end 1112, in a direction from the lumen 1106 outwards. For example, a portion of the leaflet structure 1104 adjacent the outflow end 1112 can be substantially vertical, thereby forming a commissure support 1116, such that a leaflet tab 1532a, 1532b can be positioned between the upright strut 1108 and the commissure support 1116 on each side of the upright strut 1108.

The tabs 1532a, 1532b of adjacent leaflets 1528a, 1528b can be wrapped at least partially around an upright strut 1108 and coupled together, such as by one or more sutures 1534. Coupling the leaflets together in this manner can position the suture securing the leaflets (e.g., a weak point of the valve) away from the greatest stresses due to physiologic loading, thereby minimizing the risk of leaflet failure at the suture point.

Furthermore, using the upright struts 1108 for leaflet attachment can simplify valve construction in some embodiments. For example, while some conventional surgical valves require polyester inserts in order to prevent the leaflets from being pulled through the commissure supports during pressure loading, the presently disclosed attachment methods and structures can ensure that the leaflets 1528 are not pulled through the commissure supports without requiring such inserts. However, some embodiments can include an insert or polymer stent piece at the point of leaflet attachment, as shown in FIG. 16.

FIG. 16 illustrates a section view of a leaflet attachment arrangement similar to that shown in FIG. 15, except that the embodiment of FIG. 16 includes additional sutures 1644 and also an additional insert or polymer (e.g., polyester) stent piece 1636 positioned between the cloth 1130 covering the upright strut 1108 and the sutured tabs 1632a, 1632b of the leaflets 1628a, 1628b. The polyester stent piece 1636 can, in some embodiments, carry at least a part of the leaflets' load and can substantially prevent the leaflets 1628 from pulling through the leaflet structure 1104 adjacent the commissure support 1116, in the case of, for example, fracture of an upright strut 1108.

As shown in FIGS. 15-16, leaflets can be attached to disclosed embodiments of a collapsible prosthetic heart valve in ways similar to leaflet attachment for conventional surgical valves. However, the disclosed embodiments can allow for radial compression of the prosthetic heart valve, unlike surgical valves.

Additional details regarding suitable methods of leaflet attachment are discussed in U.S. Provisional Patent Application No. 61/332,885, which is incorporated herein by reference.

Overview of Prosthetic Valve Having a Two-Piece Valve Frame

Figure 19:
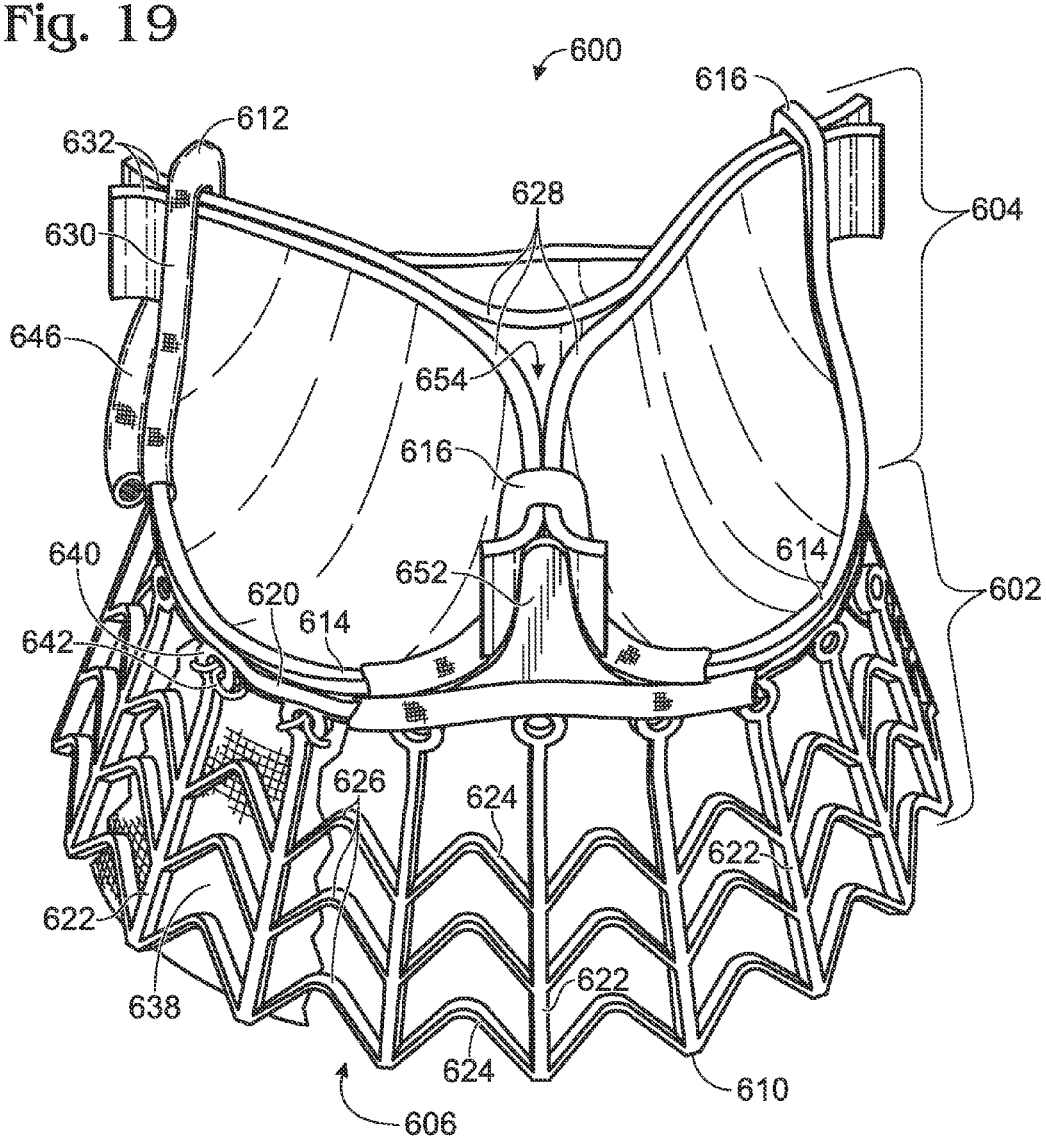
FIG. 19 shows a perspective view of one embodiment of a two piece prosthetic heart valve with leaflets partially secured.

FIG. 19 shows a prosthetic heart valve 600, which generally includes a stent portion 602 and a wireform portion 604. The stent portion 602 and the wireform portion 604 can be separate components from one another, such that no metal couples the two structures in some embodiments, thus forming a two-piece valve frame. In some embodiments, the stent portion 602 and the wireform portion 604 are only coupled together by one or more non-metallic devices or components, such as one or more of a cloth covering, a flexible skirt, a flexible leaflet support stent, and/or a sealing ring. In some embodiments, the stent portion 602 can be balloon-expandable, while the wireform portion 604 can be formed from a shape memory material.

The stent portion 602 can be formed of a plurality of vertical and horizontally-extending struts 622, 624, and the wireform portion 604 can include leaflet-supporting cusps 614 and commissure supports 616. The prosthetic valve 600, which is shown in an expanded configuration in FIG. 19, can also include a plurality of leaflets 628, a flexible skirt 638 (shown partially broken away), a sealing ring 646 (shown partially broken away), a leaflet support stent 652 (shown partially broken away), and a cloth covering 630 (shown partially broken away) over the wireform portion 604, each of which will be described in further detail below.

Figure 20:
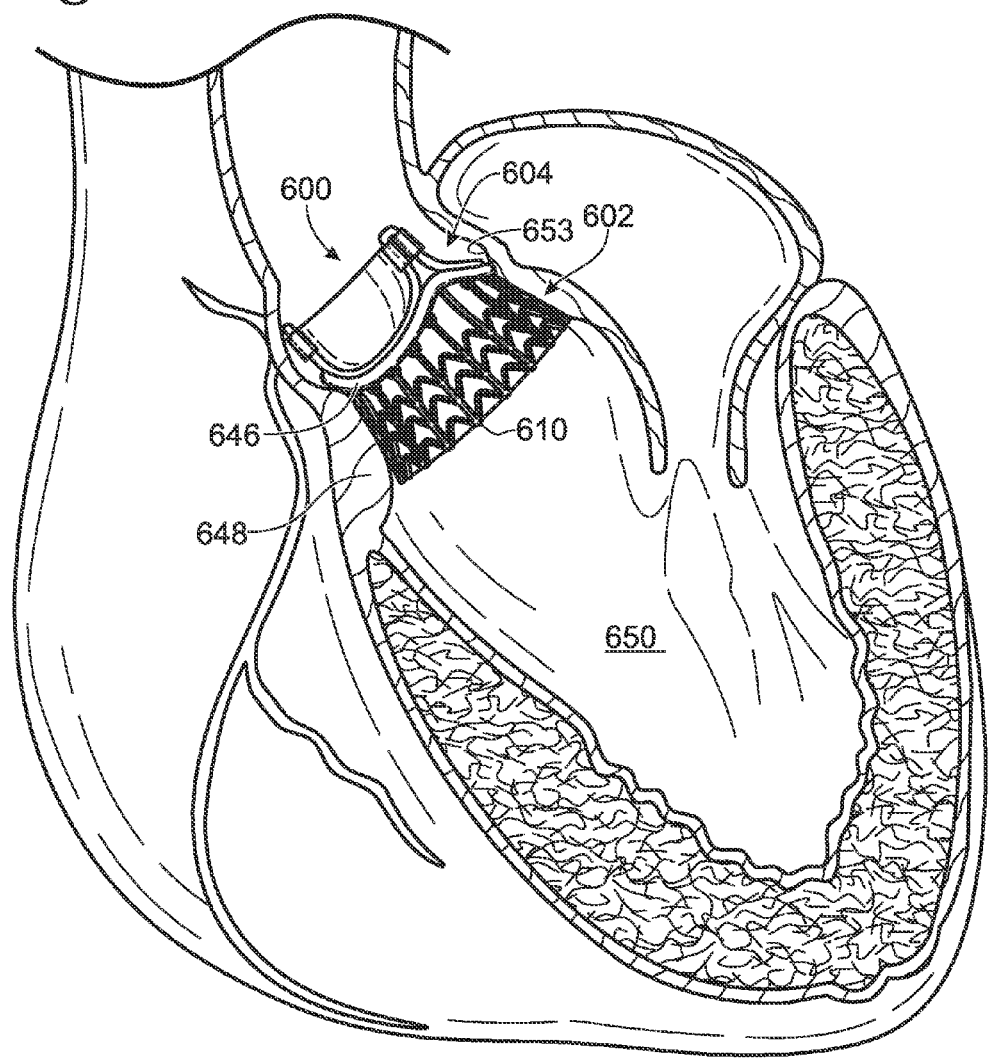
FIG. 20 shows a cutaway view of a human heart with a prosthetic heart valve implanted within the native valve annulus.

FIG. 20 shows the prosthetic heart valve 600 implanted within a patient's native valve annulus 648 (e.g., aortic valve annulus 648). As shown, the prosthetic valve 600 can be implanted such that at least a portion of the valve 600 is positioned supraannularly. For example, the wireform portion 604 can be positioned supraannularly, while the stent portion 602 is configured to anchor the prosthetic valve 600 in place within the native valve annulus 648. The stent portion 602 can be slightly flared outward at the inflow end 610, such that the stent portion 602 frictionally engages the native valve annulus 648 to prevent migration of the prosthetic valve 600. Additionally or alternatively, an optional sealing ring 646 can be provided adjacent the wireform portion 604. Said sealing ring 646 can be configured to engage the shelf 653 of the native valve annulus 648 so as to prevent migration of the prosthetic valve 600 into the ventricle 650. The sealing ring 646 can also create a seal around the prosthetic valve 600 such that substantially no blood can pass between the native valve annulus 648 and the prosthetic valve 600.

Thus, disclosed embodiments can be positioned supraannularly to a patient's native valve (e.g., the stent portion can be positioned at least partially within the annulus and at least part of the wireform portion can be positioned supraannularly). In this position, a prosthetic valve may experience significant pressure during diastole, which can push the prosthetic valve down towards the ventricle. The cusps of the wireform portion can be configured to engage with the annulus, creating a shelf to resist such pressure (e.g., the cusps of the wireform portion can have a greater diameter than the native annulus). Additionally or alternatively, the optional flexible sealing ring can be configured to rest on the native annulus when the prosthetic heart valve is deployed in place at the target site. For example, the sealing ring can have a greater diameter than the native annulus and can thereby further resist movement or dislodgement of the valve towards the ventricle.

Components of the prosthetic valve 600 will now be described in greater detail.

Leaflets

Returning to FIG. 19, the wireform portion 604 can comprise a plurality of cusps 614 configured to engage with a respective valve leaflet 628. For example, prosthetic valve 600 includes three cusps 614, each of the cusps 614 being configured to engage with one of three leaflets 628 secured to prosthetic valve 600. For example, leaflets can be secured to the cusps 614 in a manner similar to conventional surgical valves, with the leaflets being sutured to the cloth covering 630 surrounding the cusps 614. In this manner, the leaflets 628 can open when exposed to a positive pressure gradient in a fluid (e.g., blood) passing between the inflow end 610 and the outflow end 612 and close (or coapt) when exposed to a negative pressure gradient between the inflow end 610 and the outflow end 612. When the leaflets 628 are closed, as shown in FIG. 19, they can be configured to retain a central hole 654 through the center of the leaflets 628 when the valve 600 is at rest (e.g., not subject to any pressure gradient). When the leaflets 628 are subjected to a pressure gradient (e.g., after implantation in a patient's native valve annulus) the leaflets can be configured to close completely such that substantially no blood leaks through the closed leaflets during diastole. By contrast, conventional prosthetic valves configured to be radially compressed for delivery disadvantageously must be configured such that the leaflets close completely when the valve is at rest.

For illustration purposes, the leaflets 628 are shown with coupling to the prosthetic valve 600 still in progress. The leaflets 628 can each include tabs 632 at opposing ends of the leaflets. The tabs 632 can facilitate coupling of the leaflets 628 to the wireform portion 604. For example, as will be explained in further detail below in connection with FIGS. 34-35, each tab 632 can extend through an extension of one of the leaflet-supporting cusps 614 adjacent the outflow end 612 (e.g., through a respective commissure support 616). Adjacent tabs 632 can be at least partially wrapped around a post of the leaflet support stent 652 and coupled together (e.g., with sutures) around the polymer stent 652. The leaflets can additionally be secured to the frame such as by being sutured to the cloth covering 630 surrounding the cusps 614.

Examples of suitable materials for forming the valve leaflets include pericardial tissue (e.g., bovine, porcine, or cadaver pericardial tissue), biocompatible synthetic polymers, and any other suitable natural or synthetic material. While three leaflets are shown, various embodiments can comprise one, two, three, or more leaflets.

Flexible Skirt

In addition to leaflets, the prosthetic valve 600 can include a flexible skirt 638. The flexible skirt 638 can be, for example, a polyester fabric (e.g., Dacron) skirt. The flexible skirt 638 is shown coupled to the inner surface of the stent portion 602 (e.g., positioned within a lumen 606 of the stent portion 602) and can be configured to prevent leakage through the stent portion 602 once the prosthetic valve 600 is implanted within a patient's native valve. In the specific embodiment shown, the flexible skirt 638 can be coupled to one or more of the vertical struts 622, such as to circular portions 640 adjacent the circumferential strut 620 (e.g., with sutures 642). In other embodiments, skirt 638 can be coupled to the stent portion 602 in additional places and/or in alternative arrangements. In some embodiments, the skirt 638 can be coupled to a cloth covering surrounding the stent portion 602.

While FIG. 19 shows the skirt 638 positioned within the lumen 606 of the prosthetic valve 600, in some embodiments, skirt 638 can be positioned on the outer surface of the stent portion (e.g., outside of the lumen 606). In some embodiments, the prosthetic valve 600 can include a skirt on both the inside and outside surfaces of the stent portion 602. In alternative embodiments, the prosthetic valve can be provided without a flexible skirt 638.

While FIG. 19 shows only a cut-away view of the skirt 638, the skirt 638 can extend around the entire circumference of the stent portion 602. Additionally, as shown, the skirt 638 can be essentially the same height as the stent portion 602. For example, the skirt 638 can extend substantially from an inflow end 610 and towards an outflow end 612, terminating, in some embodiments, at cusp portions 614, or alternatively, adjacent a circumferential strut 620 positioned near the wireform portion 604. Thus, the skirt 638 can substantially cover the entire stent portion 602 and optionally the area of the wireform portion below the cusp portions 614. In alternative embodiments, the skirt 638 can be configured to only cover a portion of the stent portion 602.

In some embodiments, the flexible skirt 638 can extend up to meet the cloth covering 630 on the wireform portion 604 so that there is no gap between them. The flexible skirt 638 can be coupled to the cloth covering 630 so as to not impede movement of the leaflets 628 or cusps 614. The flexible skirt 638 can be coupled to the stent portion 602, the circumferential strut 620, and/or the cloth covering 630 on the wireform portion 604 so as not to impede such movement of the cusps 614. In some embodiments, the flexible skirt 638 can follow the contour of the commissure supports 616 such that everything below the leaflets 628 is substantially sealed off.

Cloth Covering

Figure 33:
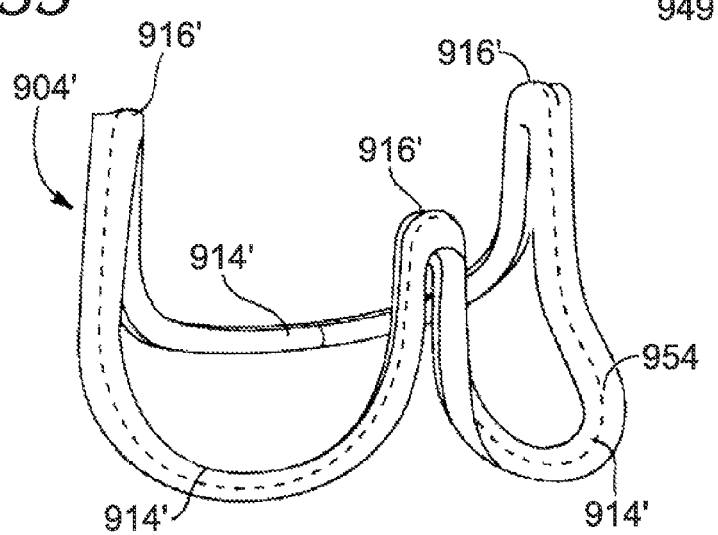
FIG. 33 shows a perspective view of one embodiment of a wireform portion covered in cloth.

The cloth covering 630 can be secured to the wireform portion 604 such that opposing longitudinal edges of the cloth 630 are brought together to form a seam external to the wireform portion 604 (see seam 954 in FIG. 33). The seam can be formed such as by suturing, adhesion, and/or other well-known cloth-edge joining techniques. The cloth covering 630 can function to provide a substrate for suturing the leaflets to. For example, the cloth covering 630 can be sutured around the wireform portion 604 and the leaflets subsequently can be sutured to the cloth 630 along the contour of the leaflet-supporting cusps 614 (e.g., on the outside of the leaflet-supporting cusps 614). The cloth 630 can also prevent the leaflets from contacting the metal of the leaflet-supporting cusps 614 and commissure supports 616, thereby potentially decreasing wear on the leaflets. Cloth covering 630 can comprise any suitable biocompatible material, such as polyester or polyethylene terephthalate.

Sealing Ring

The prosthetic heart valve 600 can include a flexible sewing ring or sealing ring structure 646, such as a tri-lobular sealing ring. The sealing ring 646 can be arranged such that sinus-shaped portions of the ring can be aligned with the cusps 614 of the wireform portion 604. The sealing ring 646 can form a tight seal between the wireform portion 604 and the stent portion 602 of disclosed prosthetic heart valve frames, can form a tight seal between the prosthetic valve and native valve annulus, and/or can provide a suture point for securing the prosthetic valve frame to the native valve annulus (in addition to or instead of using the flared stent portion to anchor the valve frame).

The sealing ring 646 can be sewn to the wireform cloth 630 through the leaflets 628 in some embodiments. In some embodiments, the leaflets 628 can be sandwiched between the wireform cloth 630 and the sealing ring 646, which may or may not include a cloth covering itself. The sealing ring 646 can be coupled to a leaflet support stent 652, around which leaflet tabs 632 can be wrapped and secured. FIG. 19 shows that the sealing ring 646 can be positioned on the wireform portion 604 adjacent the stent portion 602. The sealing ring 646 can form a tight seal between the wireform portion 604 and the stent portion 602 of disclosed prosthetic heart valve frames, and/or can provide a suture point for securing the prosthetic valve frame to the native valve annulus (in addition to or instead of using the flared stent portion to anchor the valve frame). For example, a flexible sealing ring 646 can be coupled to the wireform portion 604 in some embodiments and can be used to attach nadir sutures to the patient's annulus. In other embodiments, the sealing ring 646 can be provided without suturing it to the native valve tissue. The sealing ring 646 can additionally or alternatively be configured to provide a seal positioned between the wireform portion 604 and the stent portion 602 of the prosthetic heart valve frame, the seal being configured to enhance the effectiveness of or replace the flexible skirt discussed above.

Frame Structure

Figure 21:
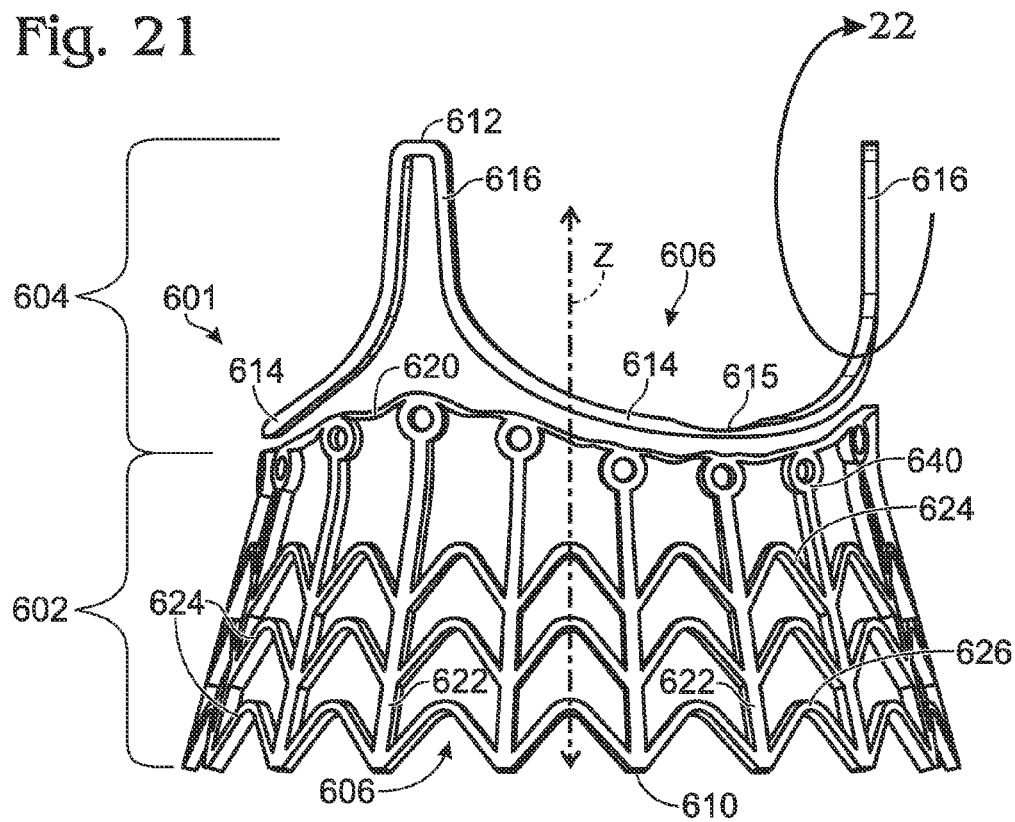
FIG. 21 shows an elevation view of one embodiment of a two piece prosthetic heart valve frame in an expanded configuration.
Figure 23:
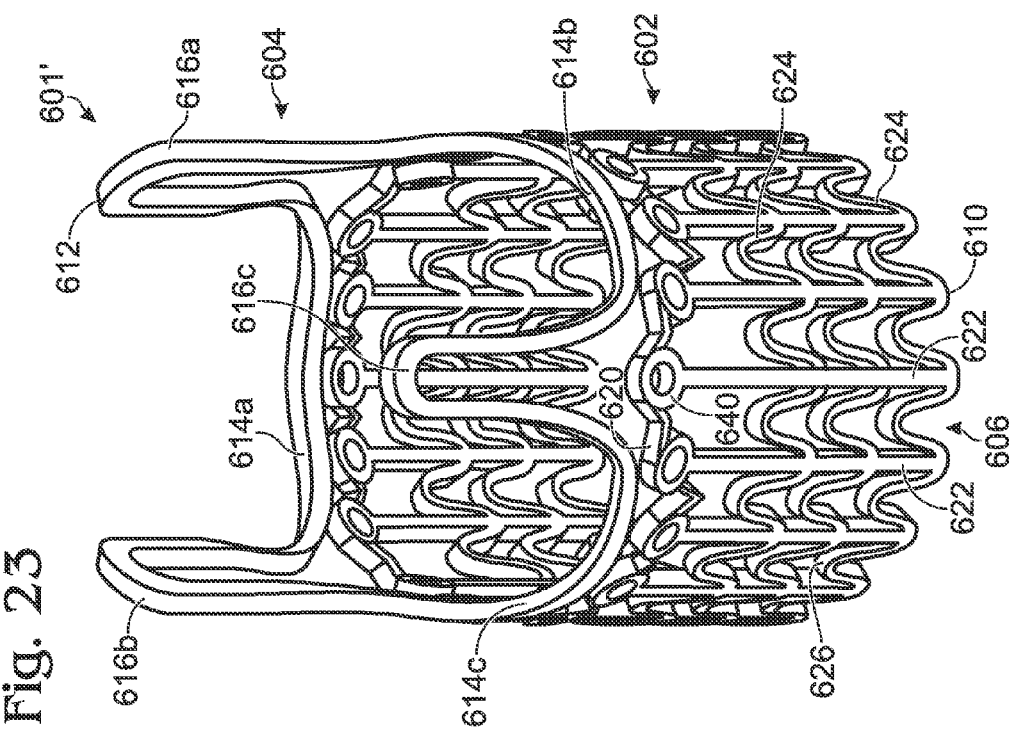
FIG. 23 is a perspective view of the prosthetic heart valve frame of FIG. 21 in a collapsed configuration.

Embodiments of a frame for use with a prosthetic heart valve will now be described. FIG. 21 illustrates the frame 601 of the prosthetic heart valve 600 of FIG. 19, with the frame still in its expanded configuration. FIG. 23 illustrates the frame 601' in a collapsed configuration (e.g., for delivery). The frame 601, 601' is shown without a plurality of leaflets, a cloth covering over a portion of the frame, a sealing ring, or a fabric or flexible skirt of another material, in order to provide a clear view of the frame.

As shown in FIG. 21, frame 601 can comprise a stent portion 602 and a wireform portion 604 (wireform portion 604 is also referred to as a leaflet support portion). In particular embodiments, the stent portion 602 and the wireform portion 604 are separate components in that they are not connected to each other by any metallic components, such as metal struts or welds. In such embodiments, the stent portion 602 can be coupled to the wireform portion 604 via other components of the valve, as further described below.

Generally, the stent portion 602 can be configured to anchor the frame 601 to a patient's native valve annulus and the wireform portion 604 can be configured to receive and support at least one valve leaflet. For example, once the prosthetic valve 600 is positioned at an implantation site, the stent portion 602 can engage an inner periphery of a body lumen (e.g., a native annulus) at the implantation site. Disclosed embodiments can engage with the native annulus via the stent portion 602 and/or a sealing ring, such as by engaging the aortic annulus, the fibrous annulus, or the aorta wall (e.g., a position downstream from the location of the native leaflets).

The stent portion 602 can define a lumen 606 therethrough. The stent portion 602 can comprise any suitable combination of struts and wires that can allow the stent portion to radially collapse to a compressed configuration for delivery and expand to an expanded configuration for operation at the implantation site. The configuration of struts and wires of the stent portion can also facilitate anchoring of the frame 601 within a patient's native valve.

As shown in FIGS. 21 and 23, the inflow end 610 corresponds to the end 610 of the stent portion 602 opposite the wireform portion 604. The outflow end 612 corresponds to the end 612 of the wireform portion 604 opposite the stent portion 602.

In some specific embodiments, each of the cusps 614 can include a thinned portion 615 (FIG. 21) configured to facilitate compression of the wireform portion 604. Each cusp 614 can include one or more thinned portions 615 that can be configured to provide the cusps 614 with greater flexibility, especially near the thinned portions 615. For example, the thinned portion 615 can be configured to deform more readily than the adjacent, thicker, areas of the cusps 614. In some embodiments, the thinned portions 615 can be positioned substantially near the center of each cusp, but other configurations are also suitable. For example, each cusp 614 could include at least two thinned portions 615 spaced apart from each other along the cusp 614. The thinned portions 615 can, for example, serve as a hinge and facilitate bending of the cusps 614 during transformation of the wireform portion 604 (and the frame 601 as a whole) from the expanded configuration shown in FIG. 21 to a compressed configuration, such as the configuration shown in FIG. 23.

As shown in FIG. 21, in an expanded configuration, the cusps 614 can be spaced apart from the stent portion 602 along a longitudinal direction defined by the lumen 606 of the stent portion 602. For example, the cusps 614 can be spaced apart from the stent portion 602 along the longitudinal axis Z in the shown expanded configuration (FIG. 21). Additionally or alternatively, the cusps 614 can be positioned further outward radially than the stent portion 602 when in the expanded configuration. For example, the cusps 614 can have a greater diameter in the expanded configuration than the circumferential strut 620. In this configuration, the cusps 614 can engage the native valve annulus (e.g., the shelf 653 of annulus 648 seen in FIG. 20).

Adjacent cusps 614 can be coupled to one another at each of a plurality of commissure supports 616 adjacent the outflow end 612. For example, adjacent cusps 614a and 614b can be coupled to one another at commissure support 616a as shown in FIG. 23. Similarly, adjacent cusps 614a and 614c can be coupled to one another at commissure support 616b, and adjacent cusps 614b and 614c can be coupled to one another at commissure support 616c.

The commissure supports 616 can lean slightly outward relative to the lumen 606 (e.g., outward relative to the central flow axis Z of the prosthetic valve frame 601) when the valve is at rest. The commissure supports 616 can alternatively be oriented to lean inwardly at a slight angle relative to the longitudinal axis Z. Alternatively, the commissure supports 616 can be substantially vertical (e.g., substantially parallel to the central flow axis) when the valve is at rest, as shown in FIG. 21.

Figure 22:
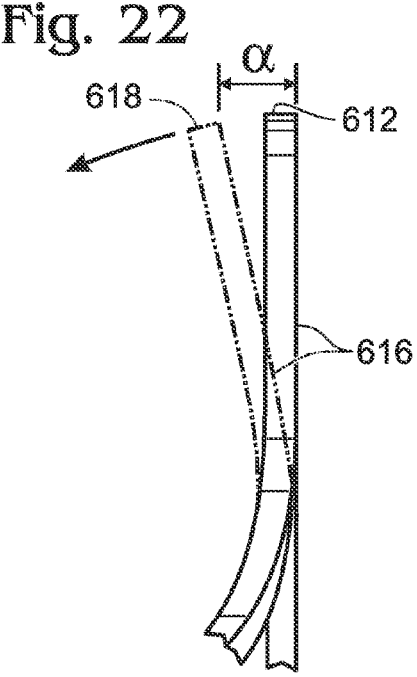
FIG. 22 shows a close-up of a portion of the prosthetic heart valve frame of FIG. 21.

At least part of the wireform portion 604 can be configured to undergo flexion (e.g., can be configured to move slightly) during normal physiologic loading when implanted in a patient's native valve. For example, as shown in FIG. 22, the commissure supports 616 (e.g., the free end of the commissure supports 616 adjacent the outflow end 612) can be configured to flex in the direction indicated by arrow 618 (e.g., radially inward) during each cardiac cycle, and likewise can be configured to move radially outward, returning to their original positions later in each cardiac cycle.

The prosthetic valve frame 601 can be positioned at the implantation site such that the cantilevered commissure supports 616 can deflect independently of the surrounding body lumen to which the valve frame 601 is secured. The ability of the commissure supports 616 to flex in this manner can allow the leaflets supported by the commissure supports 616 and cusps 614 to close more gently, thereby relieving stress on the leaflets during diastole.

In some embodiments, the wireform portion 604 can be thinner than would normally be expected, in order to optimize the movement (e.g., flexion) during pulsatile in vivo loading. Such flexion can contribute to the longevity and durability of disclosed prosthetic heart valve frames 600. The stiffness of the wireform portion 604 can be optimized such that the commissure supports 616 deflect under physiologic loading.

In some embodiments, the commissure supports 616 can be configured to deflect an amount similar to that of conventional surgical valves and an amount greater than that of conventional transcatheter valves. For example, while a conventional transcatheter valve may only flex tens of microns or less, the presently disclosed valve frames can flex up to around 1 mm or more, with flexion varying slightly with different sized valve frames. Thus, the presently disclosed prosthetic heart valve frames can flex about 10-100 times more than conventional transcatheter valves.

For example, FIG. 22 shows the deflection of a commissure support 616 under physiologic loading. The commissure support 616 can move in a cantilevered fashion radially inward and outward during each cardiac cycle. As shown in FIG. 22, the commissure support 616 can deflect radially inward a distance α. In some embodiments, α can be about 1 mm or greater.

Such flexion can be adjusted and optimized to improve hemodynamics through the valve. For example, as a result of this greater flexion, the leaflets can advantageously be arranged to retain a central hole (e.g., the three pointed star-shaped hole 654 seen in FIG. 19 where the leaflets meet in the center of the valve) when the valve is at rest (i.e., not subjected to any pressure gradient). Under physiologic loading (and flexion of the commissures), the central hole is closed completely, but the leaflets generally come together in a controlled, gentle fashion. On the other hand, conventional transcatheter valves typically cannot have such a central hole in the leaflets—the leaflets must be completely closed when the valve is at rest, because the valve is unable to flex significantly. As a result, the leaflets of traditional transcatheter valves tend to collide together more forcefully, which can disadvantageously reduce the lifespan of the prosthetic valve.

Returning to FIG. 21, the stent portion 602 of the frame 601 can be flared outward in its expanded configuration near the inflow end 610. For example, the diameter of the lumen 606 at the inflow end 610 of the stent portion 602 can be greater than the diameter of the lumen 606 of the stent portion 602 adjacent the wireform portion 604, thereby creating a flared stent portion 602. The flared configuration of the stent portion 602 can facilitate anchoring of the stent portion 602 within the patient's native valve annulus without the use of sutures (or with a reduced number of sutures as compared with conventional prosthetic heart valves). For example, as shown in FIG. 20, the flared stent portion 602 can engage with the valve annulus 648, keeping the frame 601 in position, with the wireform portion 604 being positioned distal to the annulus. Therefore, in some embodiments, at least part of the wireform portion 604 does not contact the native valve annulus once the frame 601 is implanted. For example, in some embodiments, the cusps 614 and/or a sealing ring may contact the native valve annulus, while the commissure supports 616 do not.

In some embodiments, the leaflet-supporting cusps 614 can protrude radially outward past the stent portion 602 (or at least past the upper end of stent portion 602 adjacent the cusps 614) so as to form an edge or shelf which can further discourage migration of the prosthetic heart valve frame 601 during diastole (e.g., the shelf formed by the cusps 614 could engage with or rest against the native annulus, thereby working together with the flared stent portion to prevent migration of the valve frame into the ventricle). In other words, the flared lower end of the stent portion 602 can be positioned on one side of the native annulus and can have a diameter larger than the annulus to prevent migration in one direction, while the cusps 614 can be positioned on the opposite side of the annulus and can have a diameter larger than the annulus to prevent migration in the opposite direction. For example, in embodiments where the wireform portion 604 comprises Nitinol or another superelastic material (e.g., shape memory materials), the cusps 614 can be shape set such that they are positioned further out radially than at least the end of stent portion 602 adjacent the wireform portion 604 in the expanded configuration.

In some embodiments, such as seen in FIG. 21, the frame 601 can include one or more circumferential struts 620. The circumferential strut 620 can be positioned on the stent portion 602 adjacent the wireform portion 604 and can be configured to increase the radial stiffness of the stent portion 602. Circumferential strut 620 can follow the curvature of the upper end of the stent portion 602 when the stent portion 602 is in its expanded configuration and can be bent or folded when the stent portion 602 is in its compressed configuration (sections as shown in FIG. 21 between vertical struts 622 can collapse or fold between the vertical struts 622 to facilitate crimping of the stent portion 602). The circumferential strut 620 can essentially serve as a boundary between the stent portion 602 and the wireform portion 604.

Further, the circumferential strut 620 can serve to limit the diameter of the stent portion 602 adjacent the wireform portion 604 in the expanded configuration. For example, the circumferential strut 620 can limit the diameter of the stent portion 602 at the end of the stent portion opposite the inflow end 610 so that it is no greater than the expanded diameter of the wireform portion 604. This can prevent over-expansion of the outflow end 612 of the stent portion 602 and the wireform portion 604. In some embodiments, the circumferential strut 620 can be a single continuous strut around the circumference of the stent portion 602. In some embodiments, the circumferential strut 620 can comprise a plurality of smaller struts positioned between adjacent vertical stent struts 622.

The stent portion 602 can include a plurality of vertical struts 622 that extend from the inflow end 610 towards the circumferential strut 620, if present. At least one row of horizontally-extending struts 624 can be positioned around the circumference of the stent portion 602, extending between adjacent vertical struts 622. FIG. 21 shows three rows of horizontally extending struts 624, but more or fewer rows are also possible. In the specific embodiment shown, the horizontally-extending struts 624 can be substantially U-shaped or V-shaped, with the curved portion or vertex portion 626 pointing towards the outflow end 612 of the frame 601. Bending or extending of the horizontally-extending struts 624 can decrease or increase, respectively, the distance between adjacent vertical struts 622. Thus, the horizontally-extending struts 624 can facilitate compression and expansion of the stent portion 602. In some embodiments, different rows of horizontally-extending struts 624 can be configured to expand different amounts, so as to facilitate the flared portion of the stent portion 602 near the inflow end 610. For example, the row or rows nearest the inflow end 610 can be configured to expand, elongate, or straighten more than the other row or rows of horizontally-extending struts, thereby allowing a portion of the stent portion 602 near the inflow end 610 to be flared outwards as shown in FIG. 21.

Other shapes and configurations of the stent portion are also possible. Generally, any shape or design can be provided as the stent portion of disclosed prosthetic heart valves that allow for radial compression and expansion of the stent portion. Embodiments of various stent portions can include more or fewer horizontal and/or vertical struts than are shown in the drawings. Locations, orientations, and numbers of struts can be varied to alter radial force exerted by the pre-crimped stent portion and to optimize fatigue resistance in particular embodiments.

Figure 24:
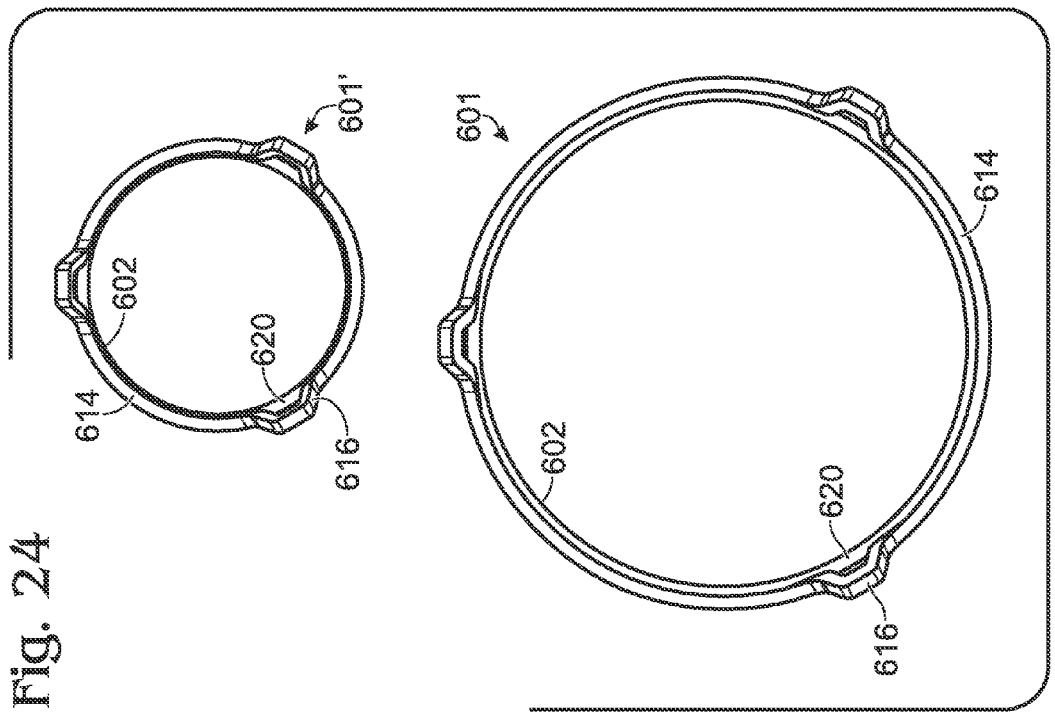
FIG. 24 is a top plan view of the collapsed prosthetic heart valve frame of FIG. 23 as compared to the expanded prosthetic heart valve frame of FIG. 21.

FIGS. 23-24 show the valve frame 601 in a collapsed configuration 601' (e.g., radially compressed for delivery). FIG. 24 shows the collapsed frame 601' next to the expanded frame 601 for an example of one relative size difference between the two configurations. In one specific example, a prosthetic valve frame can be collapsed from a 25 mm size to a 14 mm outside diameter for delivery. For example, both the stent portion and the wireform portion can be collapsed to 14 mm outer diameter or less. The wireform portion can be collapsed radially to the same diameter as a pre-crimped stent portion in some embodiments.

As shown in FIG. 23, when the valve frame 601' is radially compressed (or when the frame 601' is in a pre-crimped collapsed configuration), the circumferential strut 620 can become pinched into V-shaped sections between adjacent circular openings 640. Further, adjacent vertical struts 622 can move closer to one another as the frame 601' is collapsed (or can be closer to one another as compared to the expanded configuration). While FIG. 23 does not show thinned portions (e.g., thinned portions 615 shown in FIG. 21), in some embodiments, thinned portions of the cusps can also facilitate compression or crimping of the frame 601' to a reduced diameter for delivery.

In some embodiments, the stent portion 602 can comprise a balloon-expandable material and can be rigid or stiff enough to constrain at least the cusps 614 of the wireform portion 604 in its collapsed state without any external constraints on the wireform portion 604, such as a sheath or band around the wireform portion. For example, in embodiments where the wireform portion 604 comprises a shape memory material (e.g., Nitinol) and the stent portion 602 comprises a balloon expandable material, the wireform portion 604 can be secured to the stent portion 602 by sutures, a sealing ring, a leaflet support stent, cloth coverings, and/or some other coupling arrangement. Whatever the coupling, it can be configured such that at least the cusps 614 of the wireform portion 604 cannot be expanded beyond the stent portion 602. Furthermore, the stent portion 602 can be stiff enough in its compressed configuration that it can remain compressed despite any tendency of the wireform portion 604 to move to its unstressed, expanded configuration. Thus, the stiffness of the stent portion 602 can substantially prevent at least the cusps 614 of the wireform portion 604 from expanding without any external restraining device on the wireform portion 604. Additionally or alternatively, an external sheath or other restraining device can be used to retain at least a portion of the wireform portion 604 in its crimped configuration. For example, in some embodiments, a restraint can be positioned around all or a portion of the wireform portion. In some embodiments, a restraint can be positioned around the commissure supports 616 of the wireform portion in order to prevent premature expansion of the wireform portion 604.

Once the prosthetic valve has been positioned within a patient's valve, the balloon-expandable stent portion 602 can be expanded. As the stent portion 602 is expanded, the wireform portion 604 follows. For example, the wireform portion 604 can expand to the extent the stent portion 602 allows it to expand.

Figure 27:
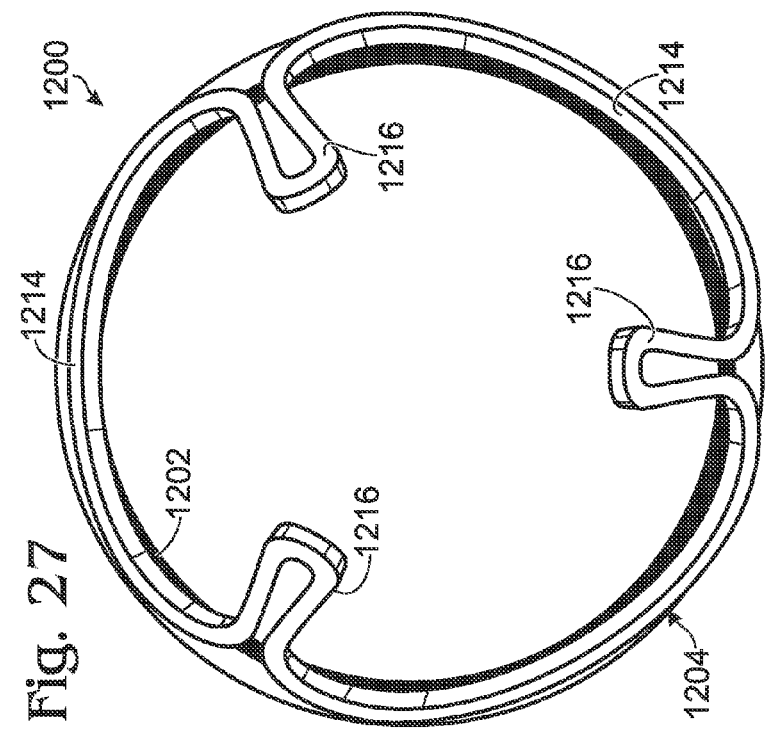
FIG. 27 shows a top plan view of the configuration shown in FIG. 26.
Figure 25:
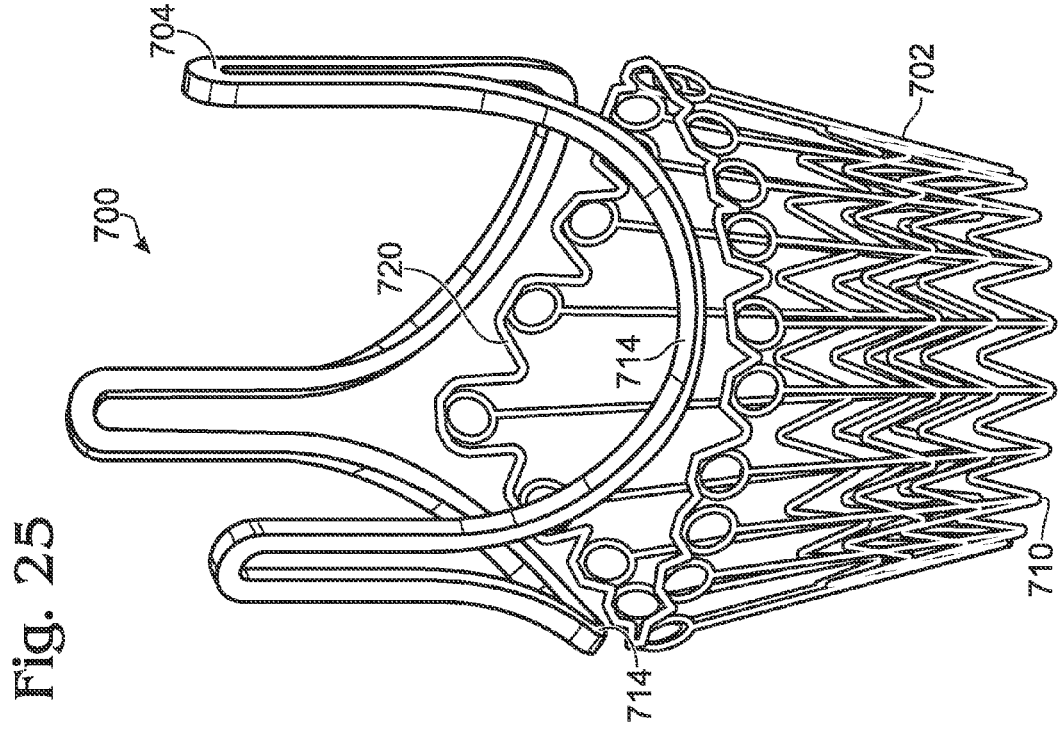
FIG. 25 shows another embodiment of a collapsed configuration of the heart valve frame of FIG. 21.
Figure 26:
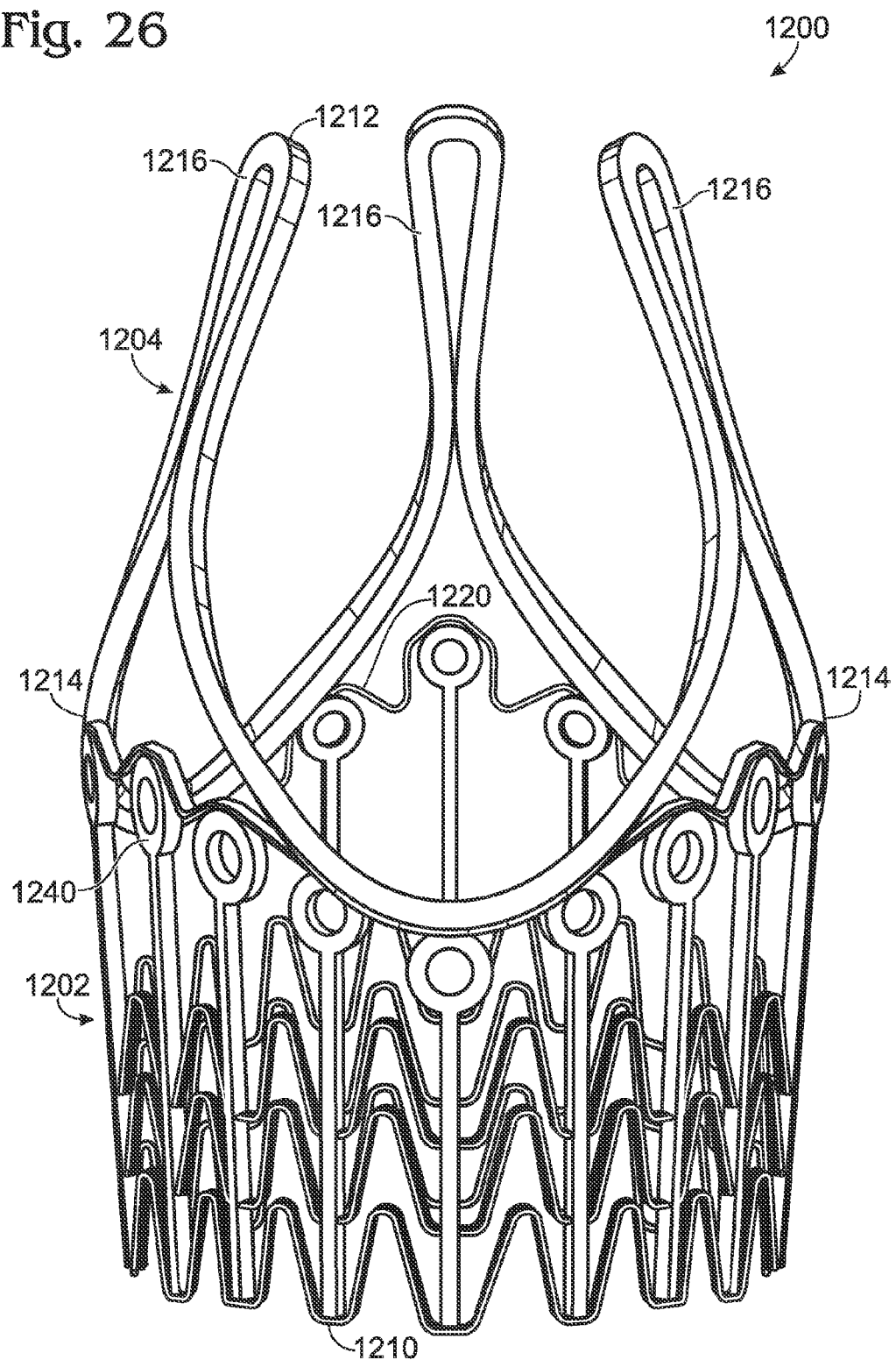
FIG. 26 shows an elevation view of the prosthetic heart valve frame of FIG. 21 in a collapsed configuration for delivery.

FIGS. 25 and 26-27 illustrate alternative collapsed configurations for disclosed embodiments of a prosthetic heart valve. For example, as shown in FIG. 25, a prosthetic heart valve frame 700 that includes a stent portion 702 and a wireform portion 704 can be compressed such that the stent portion 702 takes on a conical shape. In this embodiment, a portion of the stent portion 702 adjacent the inflow end 710 can be compressed more than a portion of the stent portion 702 adjacent the cusps 714 of the wireform portion (e.g., at the circumferential strut 720). Thus, the diameter of the stent portion 702 adjacent the inflow end 710 can be less than the diameter of the stent portion 702 adjacent the wireform portion 704, in some compressed configurations. By comparison, the stent portion 602 of FIG. 23 is substantially cylindrical when compressed, with the diameter of the stent portion 602 adjacent the inflow end 610 being substantially equal to the diameter of the stent portion 602 adjacent the cusps 614 of the wireform portion 604. In some embodiments, the frame 700 can be cut or formed in a pre-crimped, substantially cylindrical collapsed configuration, and then further crimped into a conical configuration as shown in FIG. 25.

As shown in FIGS. 26-27, in some embodiments, the tips of the commissure supports 1216 can be radially compressed more than other areas of the wireform portion 1204. For example, the commissure supports 1216 can be radially compressed towards each other adjacent the outflow end 1212, while the compressed diameter of the wireform portion 1204 can increase towards the cusps 1214 adjacent the stent portion 1202. In some embodiments, the cusps 1214 can extend slightly farther radially outward than the stent portion 1202, adjacent the circumferential strut 1220 and the circular portions 1240. In the embodiments shown, the cusps 1214 do not extend any farther radially outward than the stent portion 1202 adjacent the circumferential strut 1220. In some embodiments, the lowest points of the cusps 1214 opposite the outflow end 1212 can be positioned slightly longitudinally lower than the circumferential strut 1220 such that the cusps 1214 overlap the stent portion 1202 slightly. In other embodiments, the lowest points of the cusps 1214 opposite the outflow end 1212 can be positioned directly adjacent to or slightly longitudinally higher than the circumferential strut 1220 such that the cusps 1214 do not overlap the stent portion 1202 at all. The stent portion 1202 can be pre-crimped or compressed to a substantially cylindrical configuration as shown in FIG. 26, or to a substantially conical configuration as shown in FIG. 25.

Disclosed embodiments of a prosthetic heart valve frame can comprise any material that allows the frame to be radially collapsible and expandable. Preferable materials allow for slight flexion of at least a portion of the frame in response to pulsatile loading. Examples of suitable materials for forming the wireform portion include superelastic materials such as Nitinol, NiTiCo, NiTiCr, or alloys or combinations thereof. Examples of suitable materials for forming the stent portion include plastically deformable materials (e.g., balloon expandable materials) such as stainless steel, cobalt, chromium, titanium, or alloys or combinations of the same (e.g., CoCr alloys). Some embodiments can comprise a flexible biocompatible polymer, such as polypropylene or silicone.

Leaflet Attachment Subassembly

FIGS. 28-35 and FIGS. 40-42 illustrate components of a subassembly for attaching one or more leaflets to the prosthetic heart valve frame described above. A flexible polymer stent 1470, also referred to herein as a leaflet support stent 1470 (FIGS. 28-29), and a sealing ring insert 880 (FIG. 30) can be joined and covered by a rolled covering cloth. Alternatively, a leaflet support stent 2600 (FIGS. 40-42) and the sealing ring insert 880 (FIG. 30) can be joined and covered by a rolled covering cloth. The sealing ring insert 880 and the adjacent cloth can be suture permeable (e.g., sutures can extend through the sealing ring) and can provide an attachment region for attaching the stent portion to the wireform portion of a prosthetic valve.

Figure 28:
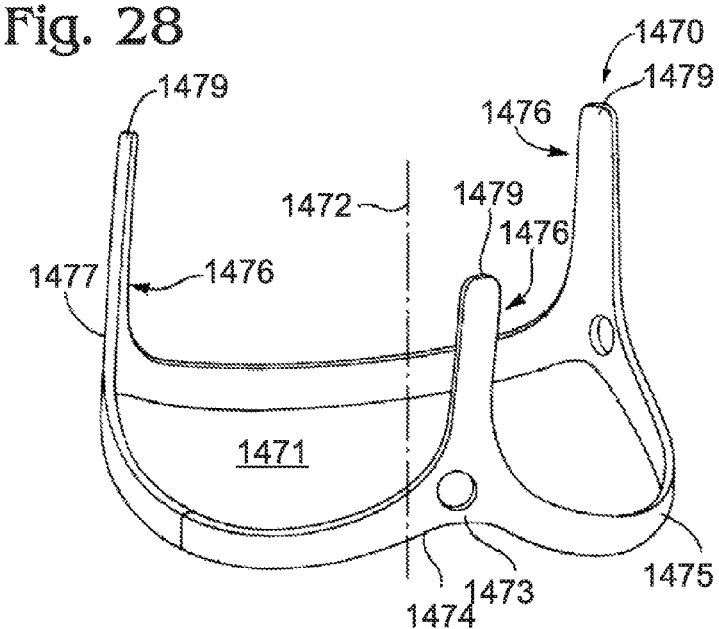
FIG. 28 shows a perspective view of one embodiment of a leaflet support stent for use with the disclosed prosthetic heart valve frame.
Figure 29:
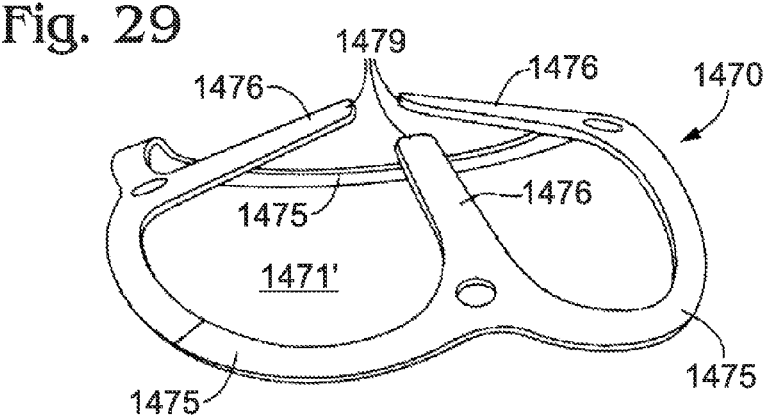
FIG. 29 shows a perspective view of the leaflet support stent of FIG. 28, in a collapsed configuration.

Referring to FIG. 28, the flexible stent 1470 is shown in a neutral position. In FIG. 29, the flexible stent 1470 is shown in a longitudinally collapsed position. The illustrated stent 1470 defines an interior, substantially cylindrical volume 1471 defining a longitudinal axis 1472 of the stent. The flexible stent 1470 comprises a circumferentially extending base member 1473. As shown, some base members 1473 can define longitudinally displaced undulations 1474 relative to, and positioned between, adjacent cusps 1475. Each of a plurality of posts 1476 extends longitudinally from a proximal end 1477 adjacent a respective undulation 1474 to a distal end defining a post tip 1479. In some instances, such a stent 1470 can be formed from any flexible biocompatible polymer, such as, for example, polypropylene. In another implementation, the stent 1470 can be made of silicone with or without a cloth core.

The primary functions of the stent 1470 are to provide additional support structure for supporting the leaflets in the tricuspid configuration under working conditions and to provide a structure to which the sealing ring can be attached. The stent is also sufficiently flexible to allow the valve to be longitudinally and/or radially collapsed to a smaller configuration for delivery.

The stent 1470 can undergo high levels of strain without suffering plastic deformation or other damage. For example, FIG. 29 illustrates an isometric view of the stent 1470 in a longitudinally collapsed position. In the illustrated position, each of the post tips 1479 has been folded radially inward from their respective neutral positions (FIG. 28) and toward the longitudinal axis 1472 of the stent. In its longitudinally collapsed position, the stent 1470 can form a substantially conically shaped interior volume 1471', as shown in FIG. 29. Although not illustrated, the stent 1470 can also be radially collapsed in a manner similar to the wireform 1204, as shown in FIGS. 26 and 27.

Figure 30:
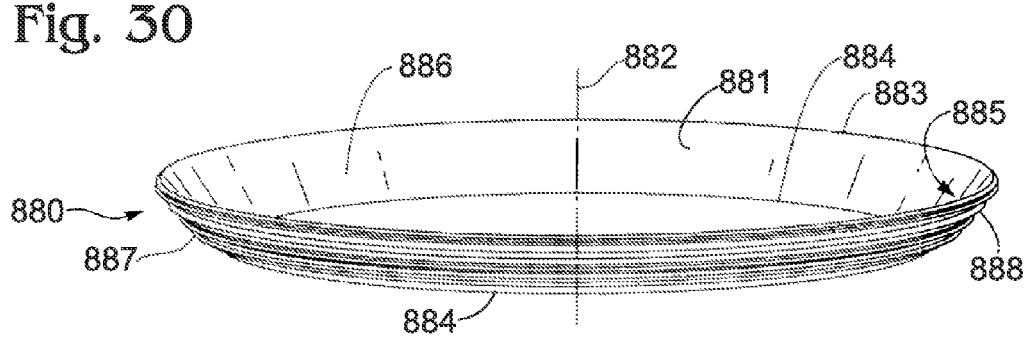
FIG. 30 shows a perspective view of one embodiment of a flexible sealing ring, without any cloth covering.

With reference to FIG. 30, an example of a sealing ring insert 880 will now be described. The body 881 of the illustrated sealing ring insert 880 comprises a frustoconical, annular body-of-rotation. In other words, the illustrated sealing ring body 881 defines a body of rotation about a sealing ring axis 882 extending longitudinally of the body. The body 881 defines a major circumference 883 having a major diameter and a minor circumference 884 having a minor diameter, and a tapering wall 885 extending between the major circumference 883 and the minor circumference 884. The wall 885 can have a relatively smooth (i.e., untextured) inner surface 886. The wall can have an outer surface 887 that is roughened, or provided with retention features (e.g., ridges, including barbs 888).

The illustrated ridges 888 formed by the outer surface 887 can provide the sealing ring portion 880 with an uneven outer contour that can engage the surrounding tissue of the implantation site. Such engagement can provide the prosthetic valve with improved purchase at the implantation site. For example, the taper of the wall 885 can facilitate placement at a desired implantation site as the minor circumference 884 first comes into contact with the surrounding tissue of the lumen. As the sealing ring 880 is urged longitudinally into the lumen, the tissue can expand and slide longitudinally of the outer surface 887. The barbs or other retention features 888 can engage the surrounding tissue and at least partially retain the sealing ring 880 within the surrounding lumen. The sealing ring can be secured in place by suturing in some embodiments, but such suturing is advantageously not required in some embodiments.

In addition, such ridges 888 can stiffen the sealing ring insert 880, adding to its resiliency. Even so, the sealing ring 880 preferably is flexible for allowing the prosthetic valve to collapse (e.g., longitudinally and/or radially collapse). In some embodiments, the sealing ring insert 880 comprises a silicone-based material, although other suture-permeable materials can be used.

A stent covering cloth (e.g., a substantially cylindrical or tubular cloth) can be axially aligned with the flexible stent 1470 and the sealing ring insert 880. In other words, the longitudinal axis of the covering cloth can be co-axially aligned with the respective longitudinal axes 1472, 882 of the stent 1470 and the sealing ring 880. The covering cloth can comprise any suitable biocompatible fabric.

Figure 31:
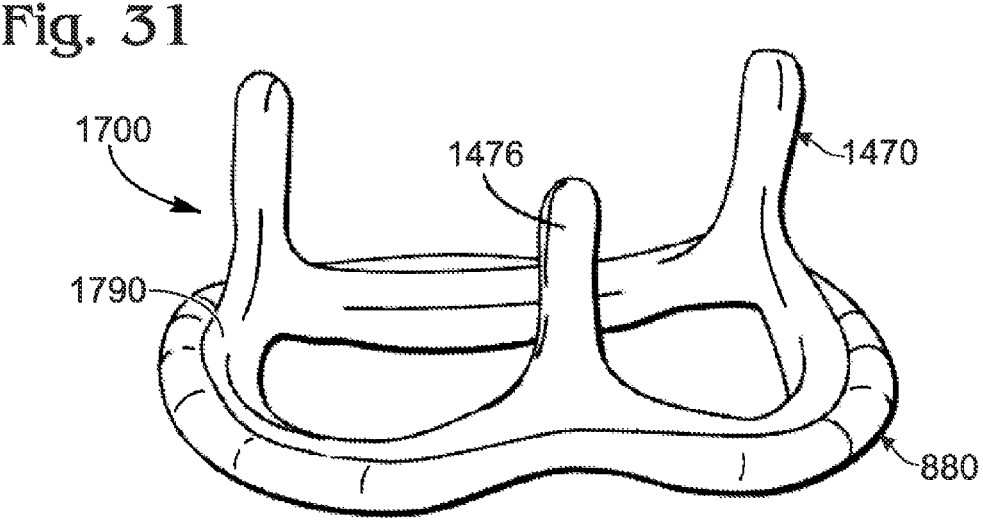
FIG. 31 shows a perspective view of one embodiment of a subassembly, which includes the leaflet support stent of FIGS. 28-29 and the sealing ring of FIG. 30, covered in cloth and coupled together.

The whole of the stent 1470 can be inserted into the interior of the tubular cloth. The sealing ring insert 880 can also be inserted into the interior of the tubular cloth. As best shown in FIG. 31, the sealing ring insert 880 and the stent 1470 can be co-centrically positioned with respect to each other such that the sealing ring 880 circumscribes the base 1473 of the stent 1470. The minor circumference 884 of the sealing ring 880 can be aligned with the lower edge of the base 1473 of the stent 1470.

Once the stent 1470 and the sealing ring insert 880 have been positioned within the tubular cloth, a free end portion of the cloth can be folded inwardly on itself. In other words, a "top" edge can be rolled inwardly toward the tube's interior and pulled through the cylindrical interior 1471 of the stent 1470 so as to line both the interior and exterior surfaces of the stent 1470 with the cloth and to juxtapose the opposing ends of the tubular cloth. FIG. 31 shows the completed subassembly 1700 of the flexible polymer stent 1470, the sealing ring 880, and the cloth covering 1790. The subassembly 1700 can be secured to a wireform portion and/or stent portion of a prosthetic heart valve, as will be described below.

FIGS. 40-42 illustrate an alternative embodiment of a subassembly 2700 (FIG. 41) that can be used in place of the subassembly 1700. FIG. 40 shows a leaflet support stent 2600 that includes a stent frame 2602 and a plurality of commissure tips 2604. The stent frame 2602 can be, for example, a flexible (e.g., radially compressible) stent frame comprising, for example, Nitinol or other superelastic material. The commissure tips 2604 can comprise, for example, a biocompatible polymer such as a polyester.

The stent frame 2602 comprises a continuous ring shaped to include three cusp support portions 2614 and three commissure portions 2608 spaced apart from one another, with a commissure portion 2608 positioned between each pair of adjacent cusp portions 2614. A commissure tip 2604 can be secured to each of the commissure portions 2608 of the stent frame 2602. For example, the commissure tips 2604 can each include one or more sewing holes 2606 through which sutures 2610 can be passed and then wrapped around the respective commissure portion 2608, thereby securing each commissure tip to each respective commissure portion 2608. Other suitable means of attachment can also be used. The leaflet support stent 2600 can have a reduced thickness as compared to conventional devices. For example, some embodiments of the leaflet support stent 2600 can be configured to have at least about a 1 mm lower profile than conventional devices. In some embodiments, while a conventional flexible support valve may have a thickness of around 1.5 mm, currently disclosed embodiments of a leaflet support valve 2600 can allow for a reduced thickness of around 0.5 mm. For example, the leaflet support stent 2600 can be formed from a wire having a thickness of around 0.5 mm. When the valve portion of a prosthetic heart valve is positioned on top of the leaflet support stent 2600, the overall height of the prosthetic valve can therefore be reduced by around 1 mm as compared to the height of the overall prosthetic valve that includes a typical conventional stent instead.

While the commissure tips 2604 are shown positioned on the inside of the stent frame 2602, they can alternatively be positioned on the outside of the stent frame 2602. In alternative embodiments, similar commissure tips can be configured to be positioned on top of the commissure portions 2608, and thus neither inside nor outside the stent frame 2602. In some embodiments, the commissure tips can be formed integrally with the stent frame. The commissure tips 2604 can be secured to the stent frame 2602 such that the commissure tips 2604 are substantially prevented from moving in the axial direction with respect to the stent frame 2602. However, the coupling of the commissure tips 2604 to the commissure portions 2608 can be configured so as not to interfere with the radial collapsibility of the overall leaflet support stent 2600.

The leaflet support stent 2600 can be combined with a sealing ring (e.g., sealing ring 880 shown in FIG. 30) and covered in cloth 2730 as described above to form a collapsible stent subassembly 2700, seen in FIG. 41. As shown in FIG. 41, the cloth-covered stent frame 2602', the cloth-covered commissure tips 2604', and the cloth-covered sealing ring 880' form the collapsible stent subassembly 2700.

FIG. 42 shows the subassembly 2700 in a radially collapsed configuration. Some embodiments of the subassembly 2700 can be radially compressed to a relatively smaller diameter than the polymer stent of FIGS. 28-29, as shown, and return to its expanded, unstressed configuration shown in FIG. 41 when any external crimping restraint is removed. When the subassembly 2700 is radially compressed, the cloth-covered commissure posts 2604' can remain substantially vertical (e.g., substantially parallel to the axial direction of the leaflet support stent) such that they do not interfere with the radial compressibility of the subassembly 2700. Thus, the subassembly 2700 can be combined with a collapsible wireform and stent portion as described herein to form a fully collapsible prosthetic heart valve. In some embodiments, the leaflet support stent 2600 and/or subassembly 2700 can be combined with (e.g., coupled to) a standalone surgical prosthetic valve or wireform portion that does not include a lower stent portion and is configured to be sutured to a patient's native valve. One such surgical prosthetic valve is disclosed in U.S. patent application No. 61/332,885 (referred to as "the '885 Application"), which is incorporated herein by reference. The use of a disclosed embodiment of the leaflet support stent 2600 with such surgical prosthetic valves as disclosed in the '885 Application can allow for use of a minimal size surgical incision when implanting such surgical valves.

Figure 32:
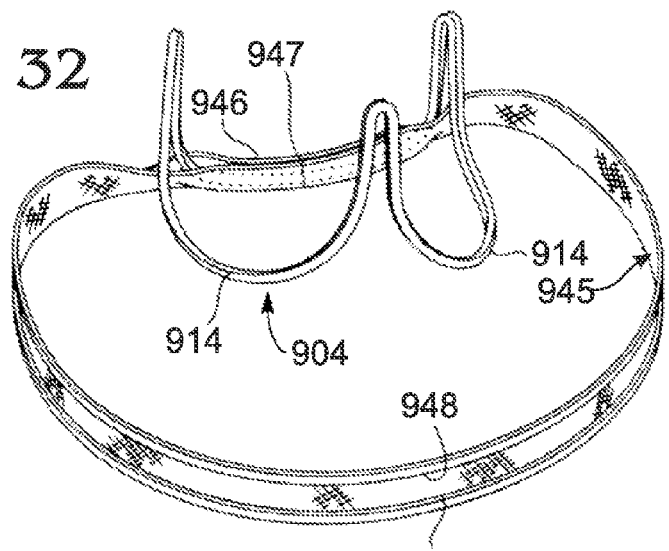
FIG. 32 shows a perspective view of one embodiment of a wireform portion in the process of being covered with cloth.

FIG. 32 shows a wireform 904 partially covered by a cloth frame cover 945. Opposing ends of a strip of cloth 945 can be brought together to form a butt joint 947. Adjacent the butt joint 947, opposing longitudinal edges 948, 949 of the cloth 945 can be wrapped around a cusp portion 914 of the wireform 904 and brought into opposing alignment with each other to form a seam 946 with the opposing edges. The seam 946 can be completed by suturing, or other well-known cloth-edge joining techniques. The cloth 945 can be wrapped around the entire wireform 904 as just described to arrive at the cloth-covered wireform 904' shown in FIG. 33. Cloth covers can be formed of any biocompatible fabric, such as, for example, polyethylene terephthalate. Other covering techniques are disclosed in U.S. Pat. No. 7,473,275, which is incorporated herein in its entirety.

Similar to the bare wireform 904, the cloth-covered wireform 904' comprises cusp regions 914' separated by commissure support portions 916.' Each commissure portion 916' extends from respective adjacent cusps 914' to respective distal ends joined to each other by an arcuate commissure tip.

Figure 34:
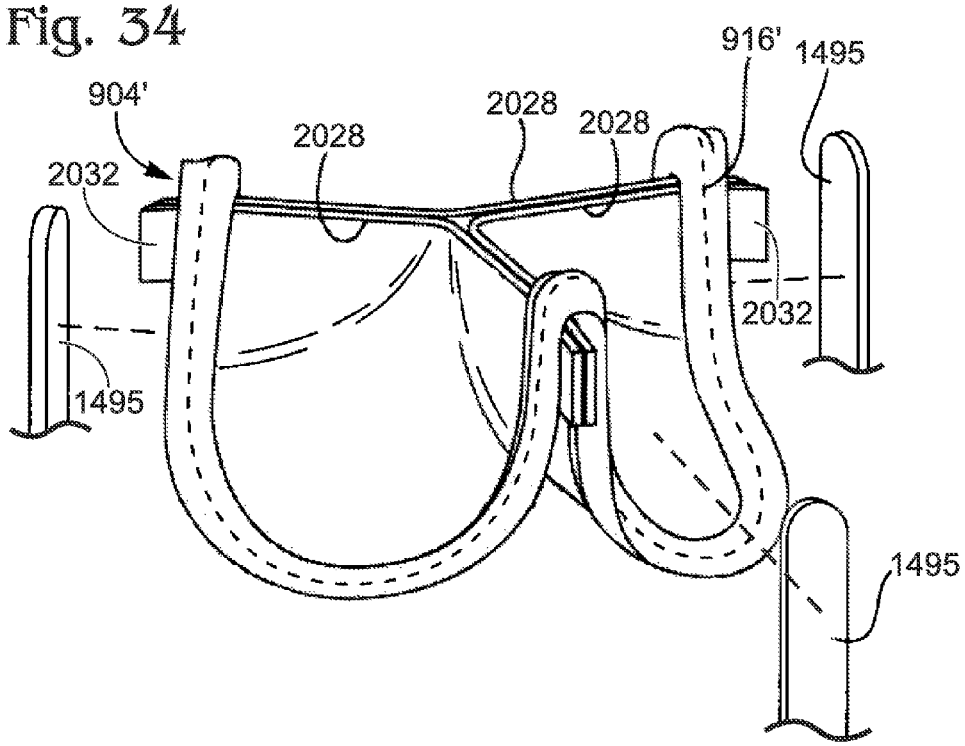
FIG. 34 shows a perspective view of placement of leaflets within the cloth covered wireform portion of FIG. 33.

FIG. 34 shows the cloth covered wireform 904' of FIG. 33, with three leaflets 2028 positioned within the wireform. Each leaflet 2028 includes two tabs 2032 positioned on opposing ends of the leaflet. Each respective tab 2032 can be aligned with a tab 2032 of an adjacent leaflet, as shown. Each pair of aligned tabs 2032 can be inserted between adjacent extensions of the wireform portion 904', near the commissure supports 916.' The tabs 2032 can then be wrapped around a respective post 1476 of a cloth covered flexible stent (e.g., flexible stent 1470 of FIG. 28 or the leaflet support stent 2600 of FIGS. 40-42). The tabs 2032 can be sutured or otherwise coupled to each other and/or to the post 1476. In this way, the leaflets 2028, the cloth covered wireform portion 904' and the cloth covered flexible stent/sealing ring subassembly (e.g., subassembly 1700 of FIG. 31 or subassembly 2700 of FIG. 41) can be coupled together. Coupling the leaflets together in this manner can position the suture securing the leaflets (e.g., a weak point of the valve) away from the greatest stresses due to physiologic loading, thereby minimizing the risk of leaflet failure at the suture point.

Figure 35:
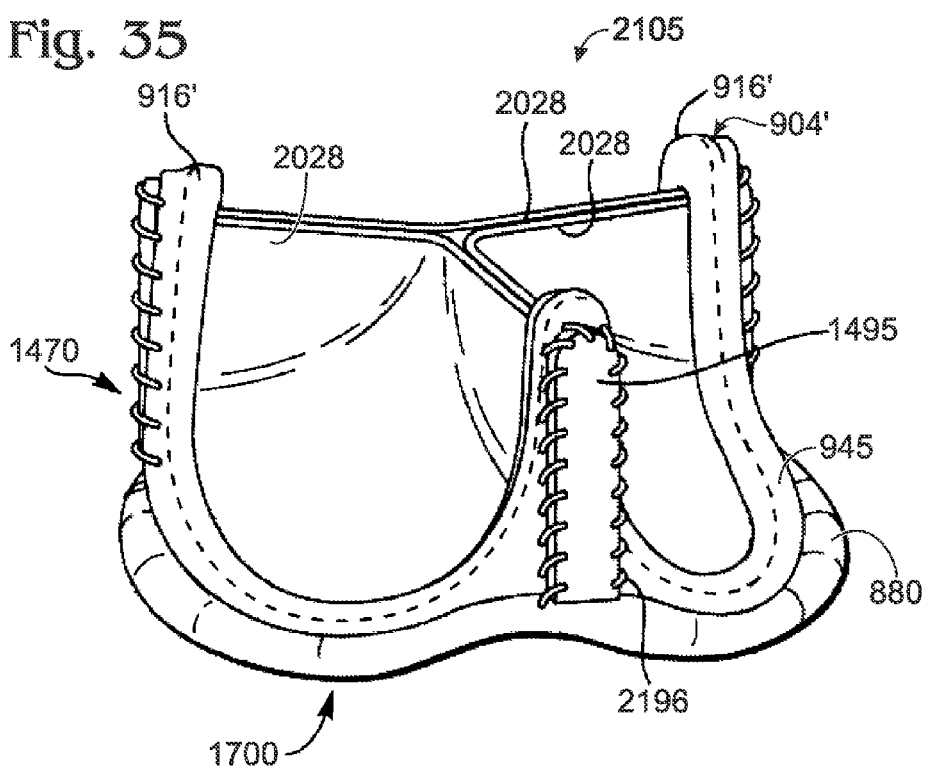
FIG. 35 shows a perspective view of the cloth covered wireform portion and leaflets of FIG. 34 in combination with the subassembly shown in FIG. 31.

As shown in FIG. 35, the flexible stent and sealing ring subassembly 1700 (or subassembly 2700) as described above can be coupled to the subassembly comprising the cloth covered wireform portion 904' and corresponding leaflets 2028 to form a valve portion 2105 of the valve. In alternative embodiments, the leaflet support stent and sealing ring subassembly 2700 as described above can be used instead of the flexible stent subassembly 1700 to form the valve portion 2105. This combination can create a fully collapsible prosthetic heart valve.

The valve portion 2105 shown in FIG. 35 can be coupled to a stent portion (e.g., stent portion 602 of FIG. 19) to assemble a prosthetic valve. For example, the sealing ring 880 can be sutured to the stent portion, such as to circular openings of vertical struts adjacent the wireform portion. The subassembly 1700 (FIG. 31) or 2700 (FIG. 41) can matingly engage a corresponding contour of the covered wireform portion 904'. In other words, as shown, for example, in FIG. 35, the cloth-covered posts 1476 of the subassembly 1700 (or the cloth-covered commissure posts 2604' of subassembly 2700) can be so sized and shaped as to overlie, or be inserted within, corresponding commissure portions 916' of the wireform 904'. Once in position, the cloth covering the posts 1476 and flexible stent 1470 can be sutured to the cloth covering 945 of the wireform 904'. Similarly, in embodiments including subassembly 2700, the cloth 2730 covering posts 2604 can be sutured to the cloth covering 945 of the wireform 904'. In addition, if desired, covers 1495 can be positioned over the exposed portions of the commissure tabs 2032 of the leaflets 2028, and secured in place with sutures 2196. The covers can be formed of any suitable biocompatible fabric or polymer.

As shown in FIGS. 34-35, leaflets can be attached to disclosed embodiments of a collapsible prosthetic heart valve in ways similar to leaflet attachment for conventional surgical valves. However, the disclosed embodiments can allow for radial compression of the prosthetic heart valve, unlike surgical valves. For example, due to the collapsibility of the individual components (e.g., the wireform portion, the leaflet support stent, the sealing ring, and the leaflets) as well as the methods of attachment, the entire valve portion 2105 can be collapsible to a collapsed state or configuration for delivery.

Delivery Methods

Disclosed embodiments of prosthetic heart valves utilizing one-piece or two-piece valve frames can be delivered to a patient's native valve annulus in a number of different ways. For example, in embodiments where the frame comprises a superelastic material, the frame can be shape set in the expanded configuration, and radially crimped (e.g., transformed into a compressed configuration and constrained within a sheath or similar structure) for delivery. Some embodiments can be delivered to a patient's valve through a small incision (e.g., a thoracotomy) and a small aortotomy. Once positioned in or near the implantation site (e.g., patient's native aortic valve annulus), the sheath can be removed, thus allowing the frame to expand to the expanded configuration (e.g., the frame can expand to the configuration shape-set before implantation). Alternatively, in embodiments with no sheath constraining the wireform portion, expansion of the stent portion (e.g., by inflating a balloon) will allow for expansion of the wireform portion as it follows the stent portion.

In embodiments where the frame comprises a non-superelastic material, the frame can be compressed or collapsed to a collapsed delivery configuration (e.g., the compressed configuration) for introduction into a patient's body. The collapsed valve can be inserted through an incision in a body lumen at an implantation site (e.g., a patient's native aortic valve annulus). The valve can then be expanded, such as by a balloon or other mechanism, once positioned in or near the native valve annulus. For example, the prosthetic valve can be crimped on a delivery catheter for delivery, positioned at the target site, and expanded by a balloon such that the stent portion anchors the prosthetic valve in place. In some embodiments, one or more sutures can be used to secure the valve in place at the implantation site. In some embodiments, no sutures are needed to secure the prosthetic valve. In some embodiments, the prosthetic valve can be positioned such that a sealing ring and/or leaflet cusps engage with the shelf of the native annulus. In some embodiments, the prosthetic valve can be radially compressed enough for transapical delivery, and thus can be delivered in a manner similar to conventional transcatheter heart valves.

Figure 36:
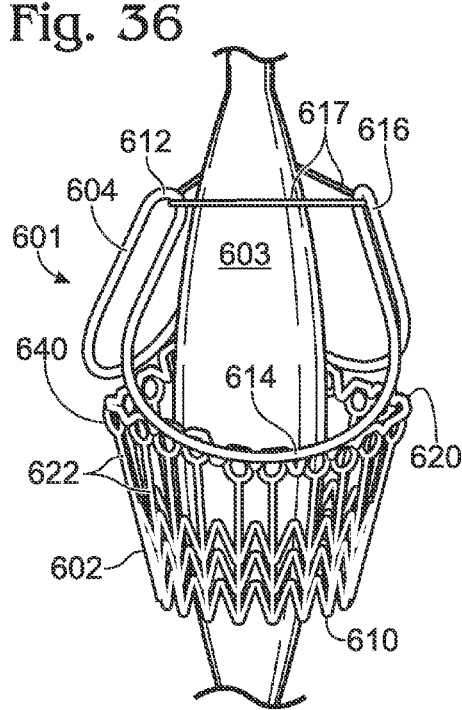
FIG. 36 shows one embodiment of a two piece prosthetic heart valve frame in a collapsed configuration positioned for delivery on an inflatable device.

By way of example, FIGS. 36-39 illustrate various stages of implantation of one embodiment of two-piece prosthetic valve frame 601, shown in a simplified form. The two-piece frame 601 includes a plastically expandable stent portion 602 and a self-expandable wireform portion 604 made of different materials which can be coupled together via one or more non-metallic components (not shown) as described above. For clarity, the frame 601 is illustrated without leaflets and other components of the valve discussed above. FIG. 36 shows the frame 601 in a collapsed configuration, positioned on a delivery device 603 (e.g., a delivery catheter having an inflatable balloon).

Figure 38:
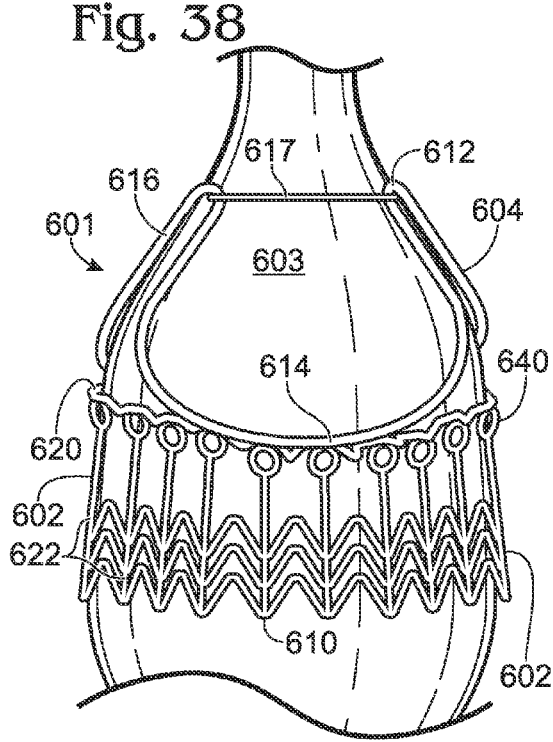
FIG. 38 shows the prosthetic heart valve frame of FIGS. 36-37 after further inflation of the inflatable device, showing full expansion of the stent portion.
Figure 37:
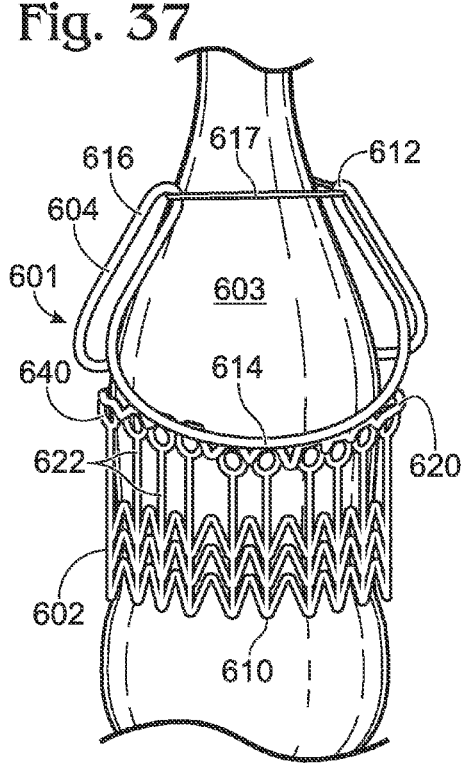
FIG. 37 shows the prosthetic heart valve frame of FIG. 36, as the inflatable device begins to be inflated.

In the embodiment shown in FIG. 36, the stent portion 602 has been collapsed into a substantially conical configuration, where the diameter of the stent portion 602 adjacent the inflow end 610 is less than the diameter of the stent portion 602 adjacent the circumferential strut 620 (e.g., opposite the inflow end 610; adjacent the wireform portion 604). Thus, adjacent vertical struts 622 are closer to one another near the inflow end than they are at the opposite end of the stent portion 602, near the wireform portion 604. The commissure supports 616 of the wireform portion 604 are shown to be compressed more in the radial direction than are the cusps 614. The wireform portion 604 can be held in this position by an external restraining sheath, valve holder, sutures, or other suitable techniques or mechanisms. As shown in FIGS. 36-38, in some embodiments, a suture 617 can be positioned to hold the commissure supports 616 in a radially compressed configuration. Alternatively or additionally, the wireform portion can be held in this compressed configuration due to its coupling to the stent portion 602. In addition, the stent portion 602 can be stiff enough to retain its compressed configuration despite any expansion force applied to it by the wireform portion 604.

Once positioned at or near the implantation site, the frame 601 can then be expanded, such as by an inflatable balloon or other mechanism. FIG. 37 illustrates partial inflation of the balloon 603. As compared to FIG. 36, the stent portion 602 has been expanded adjacent the inflow end 610, but the configuration of the circumferential strut 620 and the wireform portion 604 are substantially the same as in the delivery configuration shown in FIG. 36.

FIG. 38 shows further expansion of the balloon 603. In FIG. 38, the stent portion 602 has reached full expansion at both the inflow end 610 and adjacent the circumferential strut 620, yet the commissure supports 616 can be still at least partially compressed adjacent the outflow end 612. In some embodiments, when the circumferential strut 620 is fully expanded, the circumferential strut 620 can have an essentially flat side profile. For example, rather than being pinched into V-shaped sections as shown in FIG. 23, the circumferential strut can appear substantially straight when viewed from a side elevation it the expanded configuration.

Figure 39:
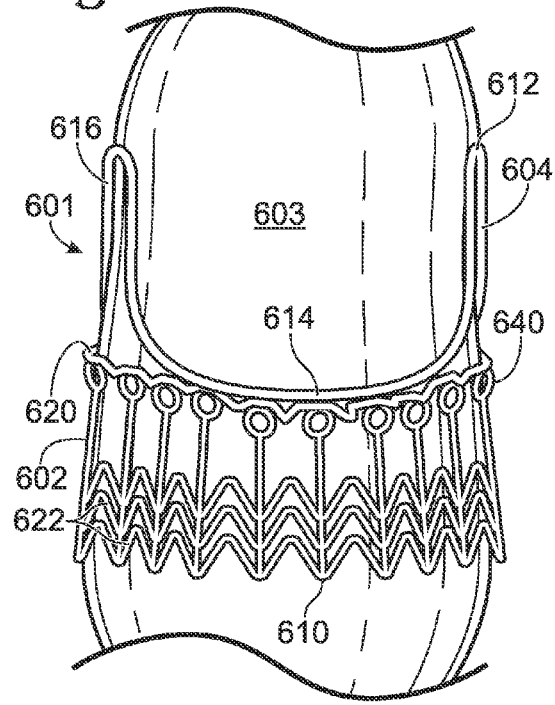
FIG. 39 shows the prosthetic heart valve frame of FIGS. 36-38 after full expansion of the wireform portion and the stent portion.

FIG. 39 shows the final expanded configuration of frame 601. For example, in some embodiments, a sheath and/or the suture 617 can be removed (e.g., by cutting or pulling the suture) from the commissure supports 616 in order to allow the wireform portion to fully self-expand as shown in FIG. 39. In some embodiments, a valve holder on the delivery system can be used to hold the commissure supports 616 in a collapsed configuration, and the commissure supports 616 can be released from the valve holder by cutting one or more sutures 617 or by some other release mechanism. In embodiments where a sheath is used to restrain the prosthetic valve, the sheath first can be partially withdrawn to allow expansion of the stent portion 602 (FIGS. 37-38), and then fully withdrawn to allow expansion of the wireform portion 604, including commissure supports 616 (FIG. 39).

In some embodiments, the stent portion 602 can be expanded an amount sufficient to anchor the prosthetic valve in place. For example, the frame 601 can be expanded until the stent portion 602 engages the patient's native valve annulus. In some embodiments, the stent portion 602 can exert force radially outward against the native valve annulus, thereby securing the prosthetic valve in place. In some embodiments, at least a portion of the prosthetic valve can be positioned supraannularly. For example, as shown in FIG. 20, a sealing ring portion 646 can be positioned supraannularly, such that it rests on the shelf 653, thereby preventing the valve from migrating into the ventricle 650.

In some embodiments, one or more sutures can be used to secure the prosthetic valve in place at the implantation site. In some embodiments, no sutures are needed to secure the prosthetic valve. In some embodiments, the prosthetic valve can be positioned such that a sealing ring and/or leaflet cusps engage with the shelf of the native annulus. In some embodiments, the prosthetic valve can be radially compressed enough for transapical delivery, and thus can be delivered in a manner similar to conventional transcatheter heart valves.

Manufacturing Methods

Methods of making and delivering a prosthetic heart valve using a one-piece or two-piece valve frame are also disclosed. For example, in one method, any of the disclosed embodiments of a prosthetic heart valve frame can be provided and at least one valve leaflet can be secured to the prosthetic heart valve. For example, the at least one valve leaflet can be secured to a one-piece prosthetic heart valve frame by passing a first and second leaflet tab between the upright strut and the wireform portion, and securing the first and second leaflet tabs to each other. Other methods of leaflet attachment for different valve frame types (e.g., frames without upright struts) are discussed above. A flexible skirt can also be secured to the stent portion, the flexible skirt being configured to prevent leakage through the stent portion.

In some methods of making a prosthetic heart valve frame, the frame can be manufactured in two pieces (e.g., the stent portion and the wireform portion can be manufactured separately), and the two pieces can be subsequently joined together, such as by crimping, welding, and/or other methods of coupling or securing together. In other embodiments, the prosthetic heart valve frame can be made as a single piece. In still other embodiments, the valve frame can be manufactured in two pieces and not joined together, other than by the other components of the valve (e.g., the sealing ring, flexible skirt, and/or cloth covering). For example, the stent portion and the wireform portion can be coupled to one another during assembly using, for example, cloth and/or sutures (e.g., sutures through the holes in the tops of upright struts).

The frame can be cut (e.g., laser cut, stamped, water-jet cut, or etched) from a sheet of material or from a hollow, metal tube of suitable material, such as Nitinol. In some embodiments, the wireform portion can be formed from a wire that has been shaped, with the two ends crimped, welded, or otherwise joined together. In some embodiments, the stent portion can be laser cut from tubing of a desire delivery diameter (e.g., pre-crimped). For example, the stent portion can be cut from 14 mm outer diameter stainless steel tubing, and in this way would be pre-crimped for delivery. In other words, in some embodiments, the stent portion can be cut or formed in its crimped or collapsed configuration. In some embodiments, the stent portion can be cut or formed in an expanded or pre-crimped configuration and then further crimped for delivery. In some embodiments, the stent portion can be crimped into a substantially conical shape for delivery. The stent portion and the wireform portion can be coupled to one another during assembly using, for example, cloth and/or sutures.

Generally, any method of forming a prosthetic heart valve frame or coupling the stent portion and wireform portion together to form a prosthetic heart valve frame can be suitable, as long as collapsibility of the prosthetic heart valve is retained. The valve frame can also be heat treated in some embodiments to, for example, form a flare at the inflow end of the stent portion. Other finishing processes can also be performed, such as microblasting and/or electropolishing.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as our invention all that comes within the scope and spirit of these claims.

I claim:

1. A prosthetic heart valve that is radially expandable from a compressed configuration to an expanded configuration, comprising:
    a balloon-expandable stent portion configured to anchor the prosthetic valve against a heart valve annulus, the stent portion defining a lumen therethrough, wherein the stent portion is radially expandable from a collapsed state to an expanded state, wherein the stent portion has a circumferential strut at an outflow end thereof having an expanded diameter in the expanded state of the stent portion, the stent portion further including an inflow end opposite the outflow end that flares outward from the outflow end in the expanded state of the stent portion;
    a plurality of valve leaflets;
    a self-expandable wireform portion that is separate from the stent portion, the wireform portion comprising a plurality of commissure supports extending in an outflow direction and the same number of cusps defining an inflow end of the wireform portion, each cusp adapted to support one of the valve leaflets, wherein the wireform portion is radially expandable from a constrained configuration to an expanded configuration where the cusps define an inflow diameter of the wireform portion, the wireform portion having a cloth covering;
    a cloth-covered flexible leaflet support stent arranged around the wireform portion and being radially collapsible and expandable along with the wireform portion, the cloth-covered leaflet support stent being attached with sutures to the cloth covering of the wireform portion;
    connecting sutures coupling the circumferential strut at the outflow end of the stent portion adjacent to an inflow end of the leaflet support stent such that the expanded diameter of the stent portion is equal to the cusp diameter;
    a sealing ring circumscribing and extending outward from the cloth-covered leaflet support stent and from the outflow end of the stent portion, and
    wherein the stiffness of the circumferential strut of the stent portion in its collapsed state is sufficient to prevent the inflow end of the wireform portion from expanding toward its expanded configuration by virtue of the outflow end of the stent portion being sutured thereto.

2. The prosthetic heart valve according to claim 1, wherein the leaflet support stent has a plurality of posts aligned with and outside of the commissure supports of the wireform portion, and wherein each valve leaflet is at least partially wrapped around a respective post of the flexible leaflet support stent.

3. The prosthetic heart valve according to claim 2, wherein each leaflet has two opposing tabs, the tabs of adjacent leaflets being configured to be coupled together at a respective commissure support.

4. The prosthetic heart valve according to claim 3, wherein at least a portion of each of the leaflet tabs is wrapped around a post of the flexible leaflet support stent.

5. The prosthetic heart valve according to claim 1, wherein each of the cusps comprises a thinned portion configured to facilitate compression of the wireform portion.

6. The prosthetic heart valve according to claim 1, wherein the stent portion comprises stainless steel, cobalt chromium, or alloys or combinations thereof, and wherein the wireform portion comprises Nitinol, NiTiCr, NiTiCo, or alloys or combinations thereof.

7. The prosthetic heart valve according to claim 1, wherein the stent portion has a series of circular openings at the outflow end thereof through which the sutures pass that couple the stent portion to the inflow end of the combination of the leaflet support stent and wireform portion.

8. The prosthetic heart valve according to claim 1, wherein when the prosthetic valve is in the compressed configuration, at least a portion of the wireform portion overlaps the circumferential strut of the stent portion.

9. The heart valve according to claim 1, wherein the leaflet support stent comprises a continuous stent frame and a plurality of separate commissure tips secured thereto that form support stent commissures.

10. A fully collapsible prosthetic heart valve that is radially expandable from a compressed configuration to an expanded configuration, comprising:
    a valve portion comprising a self-expandable wireform portion and a plurality of valve leaflets supported thereby, wherein the valve portion is radially expandable from a constrained state toward an expanded state, the valve portion including a suture-permeable sealing ring disposed around an inflow end of the wireform portion, the inflow end defining an expanded diameter in the expanded state; and a pre-crimped balloon-expandable stent portion configured to anchor the prosthetic valve against a heart valve annulus, wherein the stent portion is coupled to the valve portion via sutures connected between an outflow end of the stent portion and the inflow end of the wireform portion such that the wireform portion is in its constrained state when the stent portion is in a pre-crimped state and wherein balloon expansion of the stent portion permits expansion of the inflow end of the wireform portion to the same diameter as the stent portion outflow end.

11. The heart valve according to claim 10, wherein the valve portion further comprises a leaflet support stent having commissures to which leaflet tabs attach.

12. The heart valve according to claim 11, wherein the leaflet support stent comprises a continuous stent frame and a plurality of separate commissure tips secured thereto that form the support stent commissures.

13. The heart valve according to claim 10, wherein the stiffness of the stent portion in its pre-crimped state is sufficient to prevent the wireform portion from self-expanding to its expanded state.

14. The prosthetic heart valve according to claim 10, wherein the wireform portion comprises a plurality of commissure supports extending in an outflow direction and the same number of cusps defining an inflow end of the wireform portion, each cusp adapted to support one of the valve leaflets, and wherein each of the cusps comprises a thinned portion configured to facilitate compression of the wireform portion.

15. The prosthetic heart valve according to claim 10, wherein the stent portion has a circumferential strut at an outflow end thereof.

16. The prosthetic heart valve according to claim 15, wherein the stent portion has a series of circular openings at the outflow end thereof through which the sutures pass that connect the stent portion to the inflow end of the wireform portion, the wireform portion having a cloth covering through which the sutures pass.

17. The prosthetic heart valve according to claim 15, wherein when the prosthetic valve is in the compressed configuration, at least a portion of the wireform portion overlaps the circumferential strut of the stent portion.

\* \* \* \* \*